United States Patent
Mootha et al.

(10) Patent No.: US 11,661,586 B2
(45) Date of Patent: May 30, 2023

(54) EXTRACELLULAR REDOX ENZYME SYSTEM TO ALLEVIATE DISEASE

(71) Applicant: The General Hospital Corporation, Boston, MA (US)

(72) Inventors: Vamsi K. Mootha, Boston, MA (US); Xiaoyan Robert Bao, Berkeley, CA (US); Anupam Patgiri, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 207 days.

(21) Appl. No.: 16/769,319

(22) PCT Filed: Dec. 3, 2018

(86) PCT No.: PCT/US2018/063689
§ 371 (c)(1),
(2) Date: Jun. 3, 2020

(87) PCT Pub. No.: WO2019/112974
PCT Pub. Date: Jun. 13, 2019

(65) Prior Publication Data
US 2020/0291364 A1   Sep. 17, 2020

Related U.S. Application Data

(60) Provisional application No. 62/594,323, filed on Dec. 4, 2017, provisional application No. 62/630,093, filed on Feb. 13, 2018.

(51) Int. Cl.
| | | |
|---|---|---|
| *C12N 9/08* | (2006.01) | |
| *A61P 1/00* | (2006.01) | |
| *A61K 35/18* | (2015.01) | |
| *C12N 9/02* | (2006.01) | |
| *C12N 11/16* | (2006.01) | |
| *A61K 9/00* | (2006.01) | |
| *A61K 38/00* | (2006.01) | |

(52) U.S. Cl.
CPC ............ *C12N 9/0065* (2013.01); *A61K 35/18* (2013.01); *A61P 1/00* (2018.01); *C12N 9/0069* (2013.01); *C12N 11/16* (2013.01); *A61K 9/0019* (2013.01); *A61K 38/00* (2013.01); *C12Y 111/01006* (2013.01); *C12Y 113/12004* (2013.01)

(58) Field of Classification Search
CPC ......... A61P 1/00; A61K 35/18; A61K 9/0019; A61K 38/00; C12N 9/0065; C12N 9/0069; C12N 11/16; C12Y 111/01006; C12Y 113/12004
USPC ...................................................... 424/93.7
See application file for complete search history.

(56) References Cited

U.S. PATENT DOCUMENTS

| | | |
|---|---|---|
| 2012/0077873 A1 | 3/2012 | Zachwieja et al. |
| 2016/0354332 A1 | 12/2016 | Sabatini et al. |
| 2016/0362716 A1* | 12/2016 | Ouyang ............... C12N 9/0065 |

FOREIGN PATENT DOCUMENTS

| | | |
|---|---|---|
| WO | WO 2002/007752 | 1/2002 |
| WO | WO 2011/150241 | 12/2011 |
| WO | WO 2014/048977 | 4/2014 |
| WO | WO 2017/023855 | 2/2017 |

OTHER PUBLICATIONS

Acharya et al., "Metabolic engineering of lactate dehydrogenase rescues mice from acidosis," Sci Rep., 2014, 4:5189, 5 pages.
Agrawal et al., "Red Blood Cell-Encapsulated L-Asparaginase: Potential Therapy of Patients with Asparagine Synthetase Deficient Acute Myeloid Leukemia," Protein & Peptide Letters, 2013, 20:392-402.
Alpar et al., "Therapeutic efficacy of asparaginase encapsulated in intact erythrocytes," Biochem Pharmacol., 1985, 34(2):257-261.
Andre et al., "Fusing catalase to an alkane-producing enzyme maintains enzymatic activity by converting the inhibitory byproduct $H_2O_2$ to the cosubstrate $O_2$," Proceedings of the National Academy of Sciences of the United States of America, 2013, 110(8):3191-3196.
Bakker et al., "Blood lactate levels are superior to oxygen-derived variables in predicting outcome in human septic shock," Chest, 1991, 99(4):956-962.
Bessette et al., "Rapid isolation of high-affinity protein binding peptides using bacterial display," Protein Engineering, Design & Selection, 2004, 17(10):731-739.
Blanco et al., "Beta-lapachone micellar nanotherapeutics for non-small cell lung cancer therapy," Cancer Res, 2010, 70(10):3896-3904.
Boumezbeur et al., "The contribution of blood lactate to brain energy metabolism in humans measured by dynamic 13C nuclear magnetic resonance spectroscopy," J Neurosci., 2010, 30(42):13983-13991.
Brand et al., "LDHA-Associated Lactic Acid Production Blunts Tumor Immunosurveillance by T and NK Cells," Cell Metabolism, 2016, 24(5):657-671.
Brown et al., "Pyruvate dehydrogenase deficiency," J Med Genet., 1994, 31:875-879.
Bucher et al., "State of oxidation-reduction and state of binding in the cytosolic NADH-system as disclosed by equilibration with extracellular lactate/pyruvate in hemoglobin-free perfused rat liver," Eur J Biochem, 1972, 27:301-317.
Carpenter et al., "Glycolysis and the significance of lactate in traumatic brain injury," Front Neurosci., 2015, 9:112, 15 pages.

(Continued)

*Primary Examiner* — Jennifer M. H. Tichy
(74) *Attorney, Agent, or Firm* — Fish & Richardson P.C.

(57) ABSTRACT

Compositions comprising (i) lactate oxidase (LOX) and Catalase (CAT), preferably in a 1:1 molar ratio; or (ii) a fusion polypeptide comprising both LOX and CAT, e.g., LOXCAT, and methods of use thereof for reducing blood lactate levels, increasing blood pyruvate levels, and/or decreasing blood lactate/pyruvate ratio in a subject.

11 Claims, 18 Drawing Sheets

Specification includes a Sequence Listing.

(56) References Cited

OTHER PUBLICATIONS

Chariot et al., "Determination of the Blood Lactate: Pyruvate Ratio as a Noninvasive Test for the Diagnosis of Zidovudine Myopathy," Arthritis & Rheumatism, 1994, 37(4):583-586.

Chouchani et al., "A Unifying Mechanism for Mitochondrial Superoxide Production during Ischemia-Reperfusion Injury," Cell Metab., 2016, 23(2):254-263.

Chouchani et al., "Ischaemic accumulation of succinate controls reperfusion injury through mitochondrial ROS," Nature, 2014, 515(7527):431-435, Author Manuscript.

Cicalese et al., "Pyruvate prevents ischemia-reperfusion mucosal injury of rat small intestine," Am J Surg., 1996, 171(1):97-100; discussion 100-1.

Cremer et al., "Kinetics of blood-brain barrier transport of pyruvate, lactate and glucose in suckling, weanling and adult rats," J Neurochem., 1979, 33:439-445.

Debray et al., "Diagnostic Accuracy of Blood Lactate-to-Pyruvate Molar Ratio in the Differential Diagnosis of Congenital Lactic Acidosis," Clin Chem., 2007, 53(5):916-921.

Dennis et al., "Albumin Binding as a General Strategy for Improving the Pharmacokinetics of Proteins," J Biol Chem., 2002, 277(38):35035-35043.

Domenech et al., "L-asparaginase loaded red blood cells in refractory or relapsing acute lymphoblastic leukaemia in children and adults: results of the GRASPALL 2005-01 randomized trial," Br. J. Haematol., 2011, 153:58-65.

Donnino et al., "Initial lactate and lactate change in post-cardiac arrest: a multicenter validation study," Crit Care Med., 2014, 42(8):1804-1811, Author Manuscript.

El-Sayed et al., "Characterization of homocysteine gamma-lyase from submerged and solid cultures of Aspergillus fumigatus ASH (JX006238)," J Microbiol Biotechnol., 2013, 23(4):499-510.

EP Extended European Search Report in European Appln. No. 18885077.0, dated Aug. 20, 2021, 11 pages.

Fischer et al. "Inhibitory effect of tumor cell-derived lactic acid on human T cells," Blood, 2007, 109(9):3812-3819.

Fleischer et al., "Enzymatic Methods for Lactic and Pyruvic Acids," Standard Methods of Clinical Chemistry, 1970, 6:245-259.

Foster et al., "Blood intermediary metabolite and insulin concentrations after an overnight fast: reference ranges for adults, and interrelations," Clin Chem., 1978, 24(9):1568-1572.

Fujii et al., "Efficacy of pyruvate therapy in patients with mitochondrial disease: A semi-quantitative clinical evaluation study," Molecular Genetics and Metabolism, 2014, 112(2):133-138.

Garin et al., "Lactate catabolism by enzyme-loaded red blood cells," Biotechnol Appl Biochem., 1995, 22(3):295-303.

Gazmuri et al., "Protecting Mitochondrial Bioenergetic Function during Resuscitation from Cardiac Arrest," Crit Care Clin., 2012, 28(2):245-270, Author Manuscript.

Haas et al., "The In-Depth Evaluation of Suspected Mitochondrial Disease," Mol Genet Metab., 2008, 94(1):16-37, Author Manuscript.

Haigis et al., "Mammalian sirtuins-emerging roles in physiology, aging, and calorie restriction," Genes & Development, 2006, 20:2913-2921.

Halestrap, "The monocarboxylate transporter family—Structure and functional characterization," IUBMB Life, 2012, 64(1):1-9.

Hamarat Baysal et al., "Encapsulation of catalase and PEG-catalase in erythrocyte," Art. Cells, Blood Subs., Immob. Biotech., 2001, 29(5):359-366.

Huckabee, "Relationships of pyruvate and lactate during anaerobic metabolism. I. Effects of infusion of pyruvate or glucose and of hyperventilation," J Clin Invest., 1958, 37(2):244-254.

Hui et al., "Glucose feeds the TCA cycle via circulating lactate," Nature, 2017, 551(7678):115-118, Author Manuscript.

Hung et al., "Imaging cytosolic NADH-NAD(+) redox state with a genetically encoded fluorescent biosensor," Cell Metabolism, 2011, 14(4):545-554.

Hwang et al., "Pharmacological stimulation of NADH oxidation ameliorates obesity and related phenotypes in mice," Diabetes, 2009, 58:965-974.

Ihler et al., "Enzymatic degradation of uric acid by uricase-loaded human erythrocytes," The Journal of Clinical Investigation, 1975, 56:595-602.

Jain et al., "Hypoxia as a therapy for mitochondrial disease," Science, 2016, 352:54-61.

Jiang et al., "Impaired Cerebral Mitochondrial Oxidative Phosphorylation Function in a Rat Model of Ventricular Fibrillation and Cardiopulmonary Resuscitation," Biomed Res Int., 2014, 2014:192769, 10 pages.

Kalnenieks et al., "Membrane D-lactate oxidase in Zymomonas mobilis: evidence for a branched respiratoiy chain," FEMS Microbiol Lett., 1998, 168(1):91-97.

Khutornenko et al., "Pyrimidine biosynthesis links mitochondrial respiration to the p53 pathway," Proceedings of the National Academy of Sciences of the United States of America, 2010, 107(29):12828-12833.

King et al., "Human cells lacking mtDNA: repopulation with exogenous mitochondria by complementation," Science, 1989, 246(4929):500-503.

Kintu-Luwaga et al., "Serum lactate and phosphate as biomarkers of intestinal ischemia in a Ugandan tertiary hospital: a cross-sectional study," Int J Emerg Med., 2013, 6:44, 7 pages.

Knudsen et al., "Kinetic Analysis of the Human Blood-Brain Barrier Transport of Lactate and Its Influence by Hypercapnia," J Cereb Blood Flow Metab., 1991, 11:581-586.

Koivisto et al., "Chronic Pyruvate Supplementation Increases Exploratory Activity and Brain Energy Reserves in Young and Middle-Aged Mice," Front Aging Neurosci., 2016, 8:41, 14 pages.

Koul et al., "Inhibition of Akt survival pathway by a small-molecule inhibitor in human glioblastoma," Mol Cancer Ther., 2006, 5(3):637-644.

Kowlgi et al., "D-lactic acidosis: an underrecognized complication of short bowel syndrome," Gastroenterol Res Pract., 2015, 2015:476215, 8 pages.

Kwon et al., "L-Asparaginase encapsulated intact erythrocytes for treatment of acute lymphoblastic leukemia (ALL)," Journal of Controlled Release, 2009, 139:182-189.

Legault et al., "A Metabolic Signature of Mitochondrial Dysfunction Revealed through a Monogenic Form of Leigh Syndrome," Cell Reports, Nov. 2015, 13:981-989.

Li et al., "Crystallographic study on the interaction of L-lactate oxidase with pyruvate at 1.9 Angstrom resolution," Biochemical and Biophysical Research Communications. 2007, 358:1002-1007.

Lin et al., "Calorie restriction extends yeast life span by lowering the level of NADH," Genes & Development, 2004, 18:12-16.

Ling et al., "D-Lactate altered mitochondrial energy production in rat brain and heart but not liver," Nutr Metab., 2012, 9:6.

Martin et al., "Rebuilt AAA+ motors reveal operating principles for ATP-fuelled machines," Nature, 2005, 437:1115-1120.

Martinus et al., "Growth of rho 0 human Namalwa cells lacking oxidative phosphorylation can be sustained by redox compounds potassium ferricyanide or coenzyme Q10 putatively acting through the plasma membrane oxidase," Biochem Mol Biol Int., 1993, 31(6):997-1005.

Mashburn et al., "Tumor Inhibitory Effect of L-Asparaginase from *Escherichia coli*," Arch. Biochem. Biophys., 1964 105:450-452.

Melik-Adamyan et al., "Substrate flow in catalases deduced from the crystal structures of active site variants of HPII from *Escherichia coli*," Proteins, 2001, 44:270-281.

Miller et al., "Regional Kinetic Constants for Blood-Brain Barrier Pyruvic Acid Transport in Conscious Rats by the Monocarboxylic Acid Carrier," J Neurochem., 1986, 46(5):1412-1416.

Mizock et al., "Lactic acidosis in critical illness," Crit Care Med., 1992, 20(1):80-93.

Morais et al., "On the contribution of the mitochondrial genome to the growth of Chinese hamster embryo cells in culture," Can J Biochem., 1982, 60(3):290-294.

Moro et al., "Beneficial effects of sodium or ethyl pyruvate after traumatic brain injury in the rat," Exp Neurol., 2010, 225(2):391-401, Author Manuscript.

(56) References Cited

OTHER PUBLICATIONS

Mukherjee et al., "Prolonged Prophylactic Protection from Botulism with a Single Adenovirus Treatment Promoting Serum Expression of a VHH-Based Antitoxin Protein," PLoS ONE, 2014, 9(8):e106422, 13 pages.
Muller et al., "Use of L-asparaginase in childhood ALL," Crit Rev Oncol Hematol., 1998, 28(2):97-113.
Muzykantov, "Drug delivery by red blood cells: vascular carriers designed by mother nature," Expert Opin Drug Deliv., 2010, 7(4):403-427, Author Manuscript.
Nordmark et al., "Cerebral energy failure following experimental cardiac arrest: Hypothermia treatment reduces secondary lactate/pyruvate-ratio increase," Resuscitation, 2009, 80(5):573-579.
Patgiri et al., "An engineered enzyme that targets circulating lactate to alleviate intracellular NADH:NAD+ imbalance," Nat. Biotechnol., 2020, 38(3):309-313.
Pink et al., "NAD(P)H:Quinone oxidoreductase activity is the principal determinant of beta-lapachone cytotoxicity," J Biol Chem, 2000, 275(8):5416-5424.
Pisal et al., "Delivery of therapeutic proteins," J Pharm Sci., 2010, 99(6):2557-2575, Author Manuscript.
Quintana et al., "Complex I deficiency due to loss of Ndufs4 in the brain results in progressive encephalopathy resembling Leigh syndrome," Proceedings of the National Academy of Sciences of the United States of America, 2010, 107(24):10996-11001.
Ross et al., "High brain lactate is a hallmark of aging and caused by a shift in the lactate dehydrogenase A/B ratio," Proceedings of the National Academy of Sciences of the United States of America, 2010, 107(46):20087-20092.
Ryou et al., "Pyruvate Protects the Brain Against Ischemia-Reperfusion Injury by Activating the Erythropoietin Signaling Pathway," Stroke, 2012, 43(4):1101-1107.
Seheult et al., "Lactic acidosis: an update," Clin Chem Lab Med., 2017, 55(3):322-333.
Shaham et al., "A plasma signature of human mitochondrial disease revealed through metabolic profiling of spent media from cultured muscle cells," Proceedings of the National Academy of Sciences of the United States of America, 2010, 107(4):1571-1575.
Sharma et al., "Pyruvate enhances neurological recovery following cardiopulmonary arrest and resuscitation," Resuscitation, 2008, 76:108-119, Author Manuscript.
Sharma et al., "Pyruvate improves cardiac electromechanical and metabolic recovery from cardiopulmonary arrest and resuscitation," Resuscitation, 2005, 66:71-81.
Shi et al., "Engineered red blood cells as carriers for systemic delivery of a wide array of functional probes," Proceedings of the National Academy of Sciences of the United States of America, Jul. 2014, 111(28):10131-10136.
Smith et al., "Lactate/H+ uptake by red blood cells during exercise alters their physical properties," Eur J Appl Physiol Occup Physiol., 1996, 75:54-61.
Taurino et al., "Comparative study of three lactate oxidases from Aerococcus viridans for biosensing applications," Electrochimica Acta, 2013, 93:72-79.
Timofeev et al., "Cerebral extracellular chemistry and outcome following traumatic brain injury: a microdialysis study of 223 patients," Brain, 2011, 134:484-494.
Titov et al., "Complementation of mitochondrial electron transport chain by manipulation of the NAD+/NADH ratio," Science, 2016, 352:231-235.
Updike et al., "Asparaginase entrapped in red blood cells: action and survival," Science, 1976, 193(4254):681-683.
Vafai et al., "Mitochondrial disorders as windows into an ancient organelle," Nature, 2012, 491:374-383.
Vafai et al., "Natural Product Screening Reveals Naphthoquinone Complex I Bypass Factors," PloS One, 2016, 11:e0162686, 13 pages.
von Kleist-Retzow et al., "Impaired mitochondrial Ca2+ homeostasis in respiratory chain-deficient cells but efficient compensation of energetic disadvantage by enhanced anaerobic glycolysis due to low ATP steady state levels," Exp Cell Res., 2007, 313(14):3076-3089.
Waugh, "An overview of enzymatic reagents for the removal of affinity tags," Protein Expr Purif., 2011, 80(2): 283-293.
Williamson et al., "Hyperglycemic pseudohypoxia and diabetic complications," Diabetes, 1993, 42:801-813.
Williamson et al., "The redox state of free nicotinamide-adenine dinucleotide in the cytoplasm and mitochondria of rat liver," Biochem. J., 1967, 103:514-527.
Xiong et al., "Mitochondrial Dysfunction and Calcium Perturbation Induced by Traumatic Brain Injury," J Neurotrauma, 1997, 14:23-34.
Yan, "Pathogenesis of Chronic Hyperglycemia: From Reductive Stress to Oxidative Stress," J Diabetes Res., 2014, 2014:137919, 11 pages.
Zhang et al., "Association between mitochondrial DNA copy number and sudden cardiac death: findings from the Atherosclerosis Risk in Communities study (ARIC)," Eur Heart J., 2017, 38(46):3443-3448.
Zhao et al., "SoNar, a Highly Responsive NAD+/NADH Sensor, Allows High-Throughput Metabolic Screening of Anti-tumor Agents," Cell Metabolism, 2015, 21:777-789.
Ikeda et al., "Thiamine as a neuroprotective agent after cardiac arrest," Resuscitation, Aug. 2016, 105:138-144.
International Preliminary Report on Patentability in International Appln. No. PCT/US2018/063689, dated Jun. 9, 2020, 8 pages.
International Search Report and Written Opinion in International Appln. No. PCT/US2018/063689, dated Feb. 7, 2019, 15 pages.

\* cited by examiner

*Lactate oxidase (LOX) catalysis reaction*

*Catalase (CAT) catalysis reaction*

Overall reaction

LOXCAT construct

LOXCAT$^{mut}$ construct

★ H265A mutation
☆ R267A mutation

1 = LOXCAT loading control for WB
2 = LOXCAT in mouse blood 30 min post injection
2 = LOXCAT in mouse blood 3h post injection

SEQUENCE LISTING

```
<160> NUMBER OF SEQ ID NOS: 9

<210> SEQ ID NO 1
<211> LENGTH: 1199
<212> TYPE: PRT
<213> ORGANISM: Artificial Sequence
<220> FEATURE:
<223> OTHER INFORMATION: engineered LOXCAT fusion polypeptide

<400> SEQUENCE: 1
```

Met His His His His His Ser Ser Gly Leu Val Pro Arg Gly Ser

-continued

```
1               5                   10                  15
Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Asp Ile
            35                  40                  45

Gly Ser Glu Phe Glu Leu Ser Gln His Asn Glu Lys Asn Pro His Gln
            50                  55                  60

His Gln Ser Pro Leu His Asp Ser Ser Glu Ala Lys Pro Gly Met Asp
65                  70                  75                  80

Ser Leu Ala Pro Glu Asp Gly Ser His Arg Pro Ala Ala Glu Pro Thr
                    85                  90                  95

Pro Pro Gly Ala Gln Pro Thr Ala Pro Gly Ser Leu Lys Ala Pro Asp
                    100                 105                 110

Thr Arg Asn Glu Lys Leu Asn Ser Leu Glu Asp Val Arg Lys Gly Ser
                    115                 120                 125

Glu Asn Tyr Ala Leu Thr Thr Asn Gln Gly Val Arg Ile Ala Asp Asp
                    130                 135                 140

Gln Asn Ser Leu Arg Ala Gly Ser Arg Gly Pro Thr Leu Leu Glu Asp
145                 150                 155                 160

Phe Ile Leu Arg Glu Lys Ile Thr His Phe Asp His Glu Arg Ile Pro
                    165                 170                 175

Glu Arg Ile Val His Ala Arg Gly Ser Ala Ala His Gly Tyr Phe Gln
                    180                 185                 190

Pro Tyr Lys Ser Leu Ser Asp Ile Thr Lys Ala Asp Phe Leu Ser Asp
                    195                 200                 205

Pro Asn Lys Ile Thr Pro Val Phe Val Arg Phe Ser Thr Val Gln Gly
                    210                 215                 220

Gly Ala Gly Ser Ala Asp Thr Val Arg Asp Ile Arg Gly Phe Ala Thr
225                 230                 235                 240

Lys Phe Tyr Thr Glu Glu Gly Ile Phe Asp Leu Val Gly Asn Asn Thr
                    245                 250                 255

Pro Ile Phe Phe Ile Gln Asp Ala His Lys Phe Pro Asp Phe Val His
                    260                 265                 270

Ala Val Lys Pro Glu Pro His Trp Ala Ile Pro Gln Gly Gln Ser Ala
                    275                 280                 285

His Asp Thr Phe Trp Asp Tyr Val Ser Leu Gln Pro Glu Thr Leu His
                    290                 295                 300

Asn Val Met Trp Ala Met Ser Asp Arg Gly Ile Pro Arg Ser Tyr Arg
305                 310                 315                 320

Thr Met Glu Gly Phe Gly Ile His Thr Phe Arg Leu Ile Asn Ala Glu
                    325                 330                 335

Gly Lys Ala Thr Phe Val Arg Phe His Trp Lys Pro Leu Ala Gly Lys
                    340                 345                 350

Ala Ser Leu Val Trp Asp Glu Ala Gln Lys Leu Thr Gly Arg Asp Pro
                    355                 360                 365

Asp Phe His Arg Arg Glu Leu Trp Glu Ala Ile Glu Ala Gly Asp Phe
                    370                 375                 380

Pro Glu Tyr Glu Leu Gly Phe Gln Leu Ile Pro Glu Glu Asp Glu Phe
385                 390                 395                 400

Lys Phe Asp Phe Asp Leu Leu Asp Pro Thr Lys Leu Ile Pro Glu Glu
                    405                 410                 415

Leu Val Pro Val Gln Arg Val Gly Lys Met Val Leu Asn Arg Asn Pro
                    420                 425                 430
```

```
Asp Asn Phe Phe Ala Glu Asn Glu Gln Ala Ala Phe His Pro Gly His
        435                 440                 445

Ile Val Pro Gly Leu Asp Phe Thr Asn Asp Pro Leu Leu Gln Gly Arg
        450                 455                 460

Leu Phe Ser Tyr Thr Asp Thr Gln Ile Ser Arg Leu Gly Gly Pro Asn
465                 470                 475                 480

Phe His Glu Ile Pro Ile Asn Arg Pro Thr Cys Pro Tyr His Asn Phe
                    485                 490                 495

Gln Arg Asp Gly Met His Arg Met Gly Ile Asp Thr Asn Pro Ala Asn
                500                 505                 510

Tyr Glu Pro Asn Ser Ile Asn Asp Asn Trp Pro Arg Glu Thr Pro Pro
        515                 520                 525

Gly Pro Lys Arg Gly Gly Phe Glu Ser Tyr Gln Glu Arg Val Glu Gly
        530                 535                 540

Asn Lys Val Arg Glu Arg Ser Pro Ser Phe Gly Glu Tyr Tyr Ser His
545                 550                 555                 560

Pro Arg Leu Phe Trp Leu Ser Gln Thr Pro Phe Glu Gln Arg His Ile
                565                 570                 575

Val Asp Gly Phe Ser Phe Glu Leu Ser Lys Val Val Arg Pro Tyr Ile
                580                 585                 590

Arg Glu Arg Val Val Asp Gln Leu Ala His Ile Asp Leu Thr Leu Ala
                595                 600                 605

Gln Ala Val Ala Lys Asn Leu Gly Ile Glu Leu Thr Asp Asp Gln Leu
        610                 615                 620

Asn Ile Thr Pro Pro Asp Val Asn Gly Leu Lys Lys Asp Pro Ser
625                 630                 635                 640

Leu Ser Leu Tyr Ala Ile Pro Asp Gly Asp Val Lys Gly Arg Val Val
                645                 650                 655

Ala Ile Leu Leu Asn Asp Glu Val Arg Ser Ala Asp Leu Leu Ala Ile
                660                 665                 670

Leu Lys Ala Leu Lys Ala Lys Gly Val His Ala Lys Leu Leu Tyr Ser
        675                 680                 685

Arg Met Gly Glu Val Thr Ala Asp Asp Gly Thr Val Leu Pro Ile Ala
        690                 695                 700

Ala Thr Phe Ala Gly Ala Pro Ser Leu Thr Val Asp Ala Val Ile Val
705                 710                 715                 720

Pro Cys Gly Asn Ile Ala Asp Ile Ala Asp Asn Gly Asp Ala Asn Tyr
                725                 730                 735

Tyr Leu Met Glu Ala Tyr Lys His Leu Lys Pro Ile Ala Leu Ala Gly
                740                 745                 750

Asp Ala Arg Lys Phe Lys Ala Thr Ile Lys Ile Ala Asp Gln Gly Glu
                755                 760                 765

Glu Gly Ile Val Glu Ala Asp Ser Ala Asp Gly Ser Phe Met Asp Glu
        770                 775                 780

Leu Leu Thr Leu Met Ala Ala His Arg Val Trp Ser Arg Ile Pro Lys
785                 790                 795                 800

Ile Asp Lys Ile Pro Ala Ala Ser Gly Ala Gly Gly Ser Glu Gly Gly
                805                 810                 815

Gly Ser Glu Gly Gly Thr Ser Gly Ala Thr Asn Asn Asn Asp Ile Glu
                820                 825                 830

Tyr Asn Ala Pro Ser Glu Ile Lys Tyr Ile Asp Val Val Asn Thr Tyr
                835                 840                 845
```

-continued

```
Asp Leu Glu Glu Ala Ser Lys Val Val Pro His Gly Gly Phe Asn
    850                 855                 860
Tyr Ile Ala Gly Ala Ser Gly Asp Glu Trp Thr Lys Arg Ala Asn Asp
865                 870                 875                 880
Arg Ala Trp Lys His Lys Leu Leu Tyr Pro Arg Leu Ala Gln Asp Val
                885                 890                 895
Glu Ala Pro Asp Thr Ser Thr Glu Ile Leu Gly His Lys Ile Lys Ala
            900                 905                 910
Pro Phe Ile Met Ala Pro Ile Ala Ala His Gly Leu Ala His Thr Thr
        915                 920                 925
Lys Glu Ala Gly Thr Ala Arg Ala Val Ser Glu Phe Gly Thr Ile Met
    930                 935                 940
Ser Ile Ser Ala Tyr Ser Gly Ala Thr Phe Glu Glu Ile Ser Glu Gly
945                 950                 955                 960
Leu Asn Gly Gly Pro Arg Trp Phe Gln Ile Tyr Met Ala Lys Asp Asp
                965                 970                 975
Gln Gln Asn Arg Asp Ile Leu Asp Glu Ala Lys Ser Asp Gly Ala Thr
            980                 985                 990
Ala Ile Ile Leu Thr Ala Asp Ser Thr Val Ser Gly Asn Arg Asp Arg
        995                 1000                1005
Asp Val Lys Asn Lys Phe Val Tyr Pro Phe Gly Met Pro Ile Val
    1010                1015                1020
Gln Arg Tyr Leu Arg Gly Thr Ala Glu Gly Met Ser Leu Asn Asn
    1025                1030                1035
Ile Tyr Gly Ala Ser Lys Gln Lys Ile Ser Pro Arg Asp Ile Glu
    1040                1045                1050
Glu Ile Ala Gly His Ser Gly Leu Pro Val Phe Val Lys Gly Ile
    1055                1060                1065
Gln His Pro Glu Asp Ala Asp Met Ala Ile Lys Arg Gly Ala Ser
    1070                1075                1080
Gly Ile Trp Val Ser Asn His Gly Ala Arg Gln Leu Tyr Glu Ala
    1085                1090                1095
Pro Gly Ser Phe Asp Thr Leu Pro Ala Ile Ala Glu Arg Val Asn
    1100                1105                1110
Lys Arg Val Pro Ile Val Phe Asp Ser Gly Val Arg Arg Gly Glu
    1115                1120                1125
His Val Ala Lys Ala Leu Ala Ser Gly Ala Asp Val Val Ala Leu
    1130                1135                1140
Gly Arg Pro Val Leu Phe Gly Leu Ala Leu Gly Gly Trp Gln Gly
    1145                1150                1155
Ala Tyr Ser Val Leu Asp Tyr Phe Gln Lys Asp Leu Thr Arg Val
    1160                1165                1170
Met Gln Leu Thr Gly Ser Gln Asn Val Glu Asp Leu Lys Gly Leu
    1175                1180                1185
Asp Leu Phe Asp Asn Pro Tyr Gly Tyr Glu Tyr
    1190                1195
```

<210> SEQ ID NO 2
<211> LENGTH: 6
<212> TYPE: PRT
<213> ORGANISM: Artificial Sequence
<220> FEATURE:
<223> OTHER INFORMATION: thrombin cleavage site

<400> SEQUENCE: 2

```
Leu Val Pro Arg Gly Ser
1               5

<210> SEQ ID NO 3
<211> LENGTH: 5
<212> TYPE: PRT
<213> ORGANISM: Artificial Sequence
<220> FEATURE:
<223> OTHER INFORMATION: enterokinase/enteropeptidase cleavage site

<400> SEQUENCE: 3

Asp Asp Asp Asp Lys
1               5

<210> SEQ ID NO 4
<211> LENGTH: 752
<212> TYPE: PRT
<213> ORGANISM: Escherichia coli
<220> FEATURE:
<221> NAME/KEY: MISC_FEATURE
<223> OTHER INFORMATION: Catalase (HPII)

<400> SEQUENCE: 4

Ser Gln His Asn Glu Lys Asn Pro His Gln His Gln Ser Pro Leu His
1               5                   10                  15

Asp Ser Ser Glu Ala Lys Pro Gly Met Asp Ser Leu Ala Pro Glu Asp
                20                  25                  30

Gly Ser His Arg Pro Ala Ala Glu Pro Thr Pro Pro Gly Ala Gln Pro
            35                  40                  45

Thr Ala Pro Gly Ser Leu Lys Ala Pro Asp Thr Arg Asn Glu Lys Leu
    50                  55                  60

Asn Ser Leu Glu Asp Val Arg Lys Gly Ser Glu Asn Tyr Ala Leu Thr
65                  70                  75                  80

Thr Asn Gln Gly Val Arg Ile Ala Asp Asp Gln Asn Ser Leu Arg Ala
                85                  90                  95

Gly Ser Arg Gly Pro Thr Leu Leu Glu Asp Phe Ile Leu Arg Glu Lys
            100                 105                 110

Ile Thr His Phe Asp His Glu Arg Ile Pro Glu Arg Ile Val His Ala
    115                 120                 125

Arg Gly Ser Ala Ala His Gly Tyr Phe Gln Pro Tyr Lys Ser Leu Ser
130                 135                 140

Asp Ile Thr Lys Ala Asp Phe Leu Ser Asp Pro Asn Lys Ile Thr Pro
145                 150                 155                 160

Val Phe Val Arg Phe Ser Thr Val Gln Gly Gly Ala Gly Ser Ala Asp
                165                 170                 175

Thr Val Arg Asp Ile Arg Gly Phe Ala Thr Lys Phe Tyr Thr Glu Glu
            180                 185                 190

Gly Ile Phe Asp Leu Val Gly Asn Asn Thr Pro Ile Phe Phe Ile Gln
    195                 200                 205

Asp Ala His Lys Phe Pro Asp Phe Val His Ala Val Lys Pro Glu Pro
210                 215                 220

His Trp Ala Ile Pro Gln Gly Gln Ser Ala His Asp Thr Phe Trp Asp
225                 230                 235                 240

Tyr Val Ser Leu Gln Pro Glu Thr Leu His Asn Val Met Trp Ala Met
                245                 250                 255

Ser Asp Arg Gly Ile Pro Arg Ser Tyr Arg Thr Met Glu Gly Phe Gly
            260                 265                 270

Ile His Thr Phe Arg Leu Ile Asn Ala Glu Gly Lys Ala Thr Phe Val
```

```
              275                 280                 285
Arg Phe His Trp Lys Pro Leu Ala Gly Lys Ala Ser Leu Val Trp Asp
290                 295                 300
Glu Ala Gln Lys Leu Thr Gly Arg Asp Pro Asp Phe His Arg Arg Glu
305                 310                 315                 320
Leu Trp Glu Ala Ile Glu Ala Gly Asp Phe Pro Glu Tyr Glu Leu Gly
                325                 330                 335
Phe Gln Leu Ile Pro Glu Glu Asp Glu Phe Lys Phe Asp Phe Asp Leu
                340                 345                 350
Leu Asp Pro Thr Lys Leu Ile Pro Glu Glu Leu Val Pro Val Gln Arg
            355                 360                 365
Val Gly Lys Met Val Leu Asn Arg Asn Pro Asp Asn Phe Phe Ala Glu
370                 375                 380
Asn Glu Gln Ala Ala Phe His Pro Gly His Ile Val Pro Gly Leu Asp
385                 390                 395                 400
Phe Thr Asn Asp Pro Leu Leu Gln Gly Arg Leu Phe Ser Tyr Thr Asp
                405                 410                 415
Thr Gln Ile Ser Arg Leu Gly Gly Pro Asn Phe His Glu Ile Pro Ile
            420                 425                 430
Asn Arg Pro Thr Cys Pro Tyr His Asn Phe Gln Arg Asp Gly Met His
            435                 440                 445
Arg Met Gly Ile Asp Thr Asn Pro Ala Asn Tyr Glu Pro Asn Ser Ile
450                 455                 460
Asn Asp Asn Trp Pro Arg Glu Thr Pro Gly Pro Lys Arg Gly Gly
465                 470                 475                 480
Phe Glu Ser Tyr Gln Glu Arg Val Glu Gly Asn Lys Val Arg Glu Arg
                485                 490                 495
Ser Pro Ser Phe Gly Glu Tyr Tyr Ser His Pro Arg Leu Phe Trp Leu
            500                 505                 510
Ser Gln Thr Pro Phe Glu Gln Arg His Ile Val Asp Gly Phe Ser Phe
            515                 520                 525
Glu Leu Ser Lys Val Val Arg Pro Tyr Ile Arg Glu Arg Val Val Asp
            530                 535                 540
Gln Leu Ala His Ile Asp Leu Thr Leu Ala Gln Ala Val Ala Lys Asn
545                 550                 555                 560
Leu Gly Ile Glu Leu Thr Asp Asp Gln Leu Asn Ile Thr Pro Pro
                565                 570                 575
Asp Val Asn Gly Leu Lys Lys Asp Pro Ser Leu Ser Leu Tyr Ala Ile
                580                 585                 590
Pro Asp Gly Asp Val Lys Gly Arg Val Val Ala Ile Leu Leu Asn Asp
            595                 600                 605
Glu Val Arg Ser Ala Asp Leu Ala Ile Leu Lys Ala Leu Lys Ala
            610                 615                 620
Lys Gly Val His Ala Lys Leu Leu Tyr Ser Arg Met Gly Glu Val Thr
625                 630                 635                 640
Ala Asp Asp Gly Thr Val Leu Pro Ile Ala Ala Thr Phe Ala Gly Ala
                645                 650                 655
Pro Ser Leu Thr Val Asp Ala Val Ile Val Pro Cys Gly Asn Ile Ala
            660                 665                 670
Asp Ile Ala Asp Asn Gly Asp Ala Asn Tyr Tyr Leu Met Glu Ala Tyr
            675                 680                 685
Lys His Leu Lys Pro Ile Ala Leu Ala Gly Asp Ala Arg Lys Phe Lys
            690                 695                 700
```

```
Ala Thr Ile Lys Ile Ala Asp Gln Gly Glu Glu Gly Ile Val Glu Ala
705                 710                 715                 720

Asp Ser Ala Asp Gly Ser Phe Met Asp Glu Leu Leu Thr Leu Met Ala
            725                 730                 735

Ala His Arg Val Trp Ser Arg Ile Pro Lys Ile Asp Lys Ile Pro Ala
            740                 745                 750

<210> SEQ ID NO 5
<211> LENGTH: 20
<212> TYPE: PRT
<213> ORGANISM: Artificial Sequence
<220> FEATURE:
<223> OTHER INFORMATION: peptide linker

<400> SEQUENCE: 5

Ala Ser Gly Ala Gly Gly Ser Glu Gly Gly Gly Ser Glu Gly Gly Thr
1               5                   10                  15

Ser Gly Ala Thr
            20

<210> SEQ ID NO 6
<211> LENGTH: 270
<212> TYPE: PRT
<213> ORGANISM: Aerococcus viridans
<220> FEATURE:
<221> NAME/KEY: MISC_FEATURE
<223> OTHER INFORMATION: lactate oxidase

<400> SEQUENCE: 6

Asn Asn Asn Asp Ile Glu Tyr Asn Ala Pro Ser Glu Ile Lys Tyr Ile
1               5                   10                  15

Asp Val Val Asn Thr Tyr Asp Leu Glu Glu Glu Ala Ser Lys Val Val
            20                  25                  30

Pro His Gly Gly Phe Asn Tyr Ile Ala Gly Ala Ser Gly Asp Glu Trp
        35                  40                  45

Thr Lys Arg Ala Asn Asp Arg Ala Trp Lys His Lys Leu Leu Tyr Pro
    50                  55                  60

Arg Leu Ala Gln Asp Val Glu Ala Pro Asp Thr Ser Thr Glu Ile Leu
65              70                  75                  80

Gly His Lys Ile Lys Ala Pro Phe Ile Met Ala Pro Ile Ala Ala His
                85                  90                  95

Gly Leu Ala His Thr Thr Lys Glu Ala Gly Thr Ala Arg Ala Val Ser
            100                 105                 110

Glu Phe Gly Thr Ile Met Ser Ile Ser Ala Tyr Ser Gly Ala Thr Phe
        115                 120                 125

Glu Glu Ile Ser Glu Gly Leu Asn Gly Gly Pro Arg Trp Phe Gln Ile
    130                 135                 140

Tyr Met Ala Lys Asp Asp Gln Gln Asn Arg Asp Ile Leu Asp Glu Ala
145                 150                 155                 160

Lys Ser Asp Gly Ala Thr Ala Ile Ile Leu Thr Ala Asp Ser Thr Val
                165                 170                 175

Ser Gly Asn Arg Asp Arg Asp Val Lys Asn Lys Phe Val Tyr Pro Phe
            180                 185                 190

Gly Met Pro Ile Val Gln Arg Tyr Leu Arg Gly Thr Ala Glu Gly Met
        195                 200                 205

Ser Leu Asn Asn Ile Tyr Gly Ala Ser Lys Gln Lys Ile Ser Pro Arg
    210                 215                 220
```

```
Asp Ile Glu Glu Ile Ala Gly His Ser Gly Leu Pro Val Phe Val Lys
225                 230                 235                 240

Gly Ile Gln His Pro Glu Asp Ala Asp Met Ala Ile Lys Arg Gly Ala
            245                 250                 255

Ser Gly Ile Trp Val Ser Asn His Gly Ala Arg Gln Leu Tyr
            260                 265                 270

<210> SEQ ID NO 7
<211> LENGTH: 4
<212> TYPE: PRT
<213> ORGANISM: Artificial Sequence
<220> FEATURE:
<223> OTHER INFORMATION: peptide linker

<400> SEQUENCE: 7

Gly Gly Gly Ser
1

<210> SEQ ID NO 8
<211> LENGTH: 5
<212> TYPE: PRT
<213> ORGANISM: Artificial Sequence
<220> FEATURE:
<223> OTHER INFORMATION: peptide linker

<400> SEQUENCE: 8

Gly Gly Gly Gly Ser
1               5

<210> SEQ ID NO 9
<211> LENGTH: 14
<212> TYPE: PRT
<213> ORGANISM: Artificial Sequence
<220> FEATURE:
<223> OTHER INFORMATION: Albumin Binding Peptide (ABP)

<400> SEQUENCE: 9

Asp Ile Cys Leu Pro Arg Trp Gly Cys Leu Trp Glu Asp
1               5                   10
```

EXTRACELLULAR REDOX ENZYME SYSTEM TO ALLEVIATE DISEASE

CLAIM OF PRIORITY

This application is a § 371 National Stage Application of PCT/US2018/063689, filed Dec. 3, 2018, which claims the benefit of U.S. Provisional Patent Application Ser. Nos. 62/594,323, filed on Dec. 4, 2017, and 62/630,093, filed Feb. 13, 2018. The entire contents of the foregoing are hereby incorporated by reference.

FEDERALLY SPONSORED RESEARCH OR DEVELOPMENT

This invention was made with Government support under Grant No. GM099683 awarded by the National Institutes of Health. The Government has certain rights in the invention.

TECHNICAL FIELD

Described herein are compositions comprising (i) lactate oxidase (LOX) and Catalase (CAT), preferably in a 1:1 molar ratio; or (ii) a fusion polypeptide comprising both LOX and CAT, e.g., LOXCAT, and methods of use thereof for reducing blood lactate levels, increasing blood pyruvate levels, and/or reducing blood lactate/pyruvate and NADH/NAD+ in a subject.

BACKGROUND

There is a large class of human diseases characterized by altered reduction-oxidation (redox) balances. These diseases include mitochondrial dysfunction; disorders related to elevate lactate (e.g. lactic acidosis, cancer), and increased [NADH]/[NAD+] ratio; and aging, among others. Diseases of the mitochondrial respiratory chain occur at a frequency of roughly one in 5000 live births, and constitute the largest group of in-born errors of metabolism (Vafai and Mootha, 2012; Munnich et al., in *Scriver's Online Metabolic and Molecular Basis of Inherited Disease* (eds Valle, D. et al.) Ch. 99, dx.doi.org/10.1036/ommbid.127 (McGraw-Hill, 2006); Shoffner, in *Scriver's Online Metabolic and Molecular Basis of Inherited Disease* (eds Valle, D. et al.) Ch. 104, dx.doi.org/10.1036/ommbid.127 (McGraw-Hill, 2006)). There are currently no proven therapies for disorders related to redox imbalances. Instead, palliative care and nutritional supplements are the standard of care therapies for this disease.

SUMMARY

Provided herein are methods for reducing blood lactate levels, increasing blood pyruvate levels, and/or decreasing blood lactate/pyruvate ratio (i.e., decreasing lactate and/or increasing pyruvate) in a subject. The methods include administering to the subject a therapeutically effective amount of:
(i) lactate oxidase (LOX) and Catalase (CAT), preferably in a 1:1 molar ratio; and/or
(ii) a fusion polypeptide comprising both LOX and CAT, e.g., LOXCAT.

Also provided herein are method for treating a subject. The methods comprise (a) selecting a subject by a method comprising obtaining a blood sample from a subject; determining one or more of blood lactate levels, blood pyruvate levels, and/or blood lactate/pyruvate ratio in the sample; and selecting a subject who has a blood lactate levels above a threshold, blood pyruvate levels below a threshold, and/or a blood lactate/pyruvate ratio above a threshold; and (b) administering to the subject a treatment comprising a therapeutically effective amount of (i) lactate oxidase (LOX) and Catalase (CAT), preferably in a 1:1 molar ratio; or (ii) a fusion polypeptide comprising both LOX and CAT, e.g., LOXCAT. In some embodiments, the treatment is administered in an amount and for a time sufficient to decrease blood lactate levels below a threshold, increase blood pyruvate levels above a threshold, and/or decrease blood lactate/pyruvate ratio below a threshold.

In some embodiments, the subject has acute lactic acidosis (e.g., in sepsis); D-lactic acid toxicity (e.g., in Short bowel syndrome); a mitochondrial disorder; cancer; an ischemia-reperfusion injury (e.g., of the brain, heart, intestine, kidney, liver, or other organ); traumatic brain injury; cardiac arrest; or type 2 diabetes.

In some embodiments, the administering is by (a) red blood cell (RBC) encapsulation; (b) enzyme attachment to RBC outer surface; (c) engineered bone marrow transplant; or (d) direct injection of appropriately formulated purified enzyme.

Also provided herein are fusion polypeptides comprising lactate oxidase (LOX) and Catalase (CAT), e.g., LOXCAT. In some embodiments, the fusion polypeptide comprises an albumin binding peptide (ABP). In some embodiments, the fusion polypeptide is encapsulated in a red blood cell (RBC); attached to an RBC outer surface; or purified enzyme.

Also provided herein are compositions comprising the fusion polypeptides described herein that are formulated for administration to a subject by (a) red blood cell (RBC) encapsulation; (b) enzyme attachment to RBC outer surface; (c) engineered bone marrow transplant; (d) direct injection of appropriately formulated purified enzyme. In some embodiments, the fusion polypeptide is or comprises albumin binding peptide (ABP) modified LOXCAT.

In addition, provided herein are compositions comprising: (i) lactate oxidase (LOX) and Catalase (CAT), preferably in a 1:1 molar ratio; or (ii) a fusion polypeptide comprising both lactate oxidase (LOX) and Catalase (CAT), e.g., LOXCAT, e.g., for use in a method of reducing blood lactate levels in a subject. In some embodiments, the subject has lactic acidosis (e.g., in sepsis); D-lactic acid toxicity (e.g., in Short bowel syndrome); a mitochondrial disorder; cancer; or type 2 diabetes.

In some embodiments, the LOXCAT fusion polypeptide described herein comprises a catalase (e.g., from *E. coli*) at the N-terminus and lactate oxidase (LOX) (e.g., from *Aerococcus viridans*) at the C-terminus; the other orientation (wherein the LOX is at the N-terminus and the catalase is at the C-terminus) can also be used.

In some embodiments, the LOXCAT fusion polypeptide described herein is at least 90% identical to amino acids 45-1199 of SEQ ID NO:1.

In some embodiments, the LOXCAT fusion polypeptide comprises amino acids 45-1199 of SEQ ID NO:1.

As used herein, in the expressions "[lactate]/[pyruvate]" and "[NADH]/[NAD+]" the brackets mean that the ratios are of absolute concentrations.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used.

The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 7A shows a western blood against $His_6$ to detect $His_6$-LOXCAT in mouse blood at 30 min post-injection. FIG. 7A-1 shows $His_6$-LOXCAT standard added for comparison on western blot, whereas FIG. 7A-2 and FIG. 7A-3 show bands from blood samples at 30 min and 3 h post-injection against $His_6$ at the same molecular weight as the LOXCAT standard. (B) LOXCAT but not LOXCAT$^{mut}$ reduces [lactate]/[pyruvate] in mouse blood at 15 min post-injection.

DETAILED DESCRIPTION

The mitochondrial respiratory chain serves two major purposes in cellular metabolism. First, it generates a large proportion of the cell's energy supply ATP. Second, it oxidizes the NADH generated by other cellular metabolic pathways, most prominently the tricarboxylic acid (TCA) cycle and glycolysis, by transferring electrons from NADH to oxygen to make water. In light of these dual roles, the notable metabolic derangements arising from respiratory chain dysfunction (RCD) can lead to both energetic stress (reduced ATP production) and reductive stress (i.e., elevated NADH/NAD$^+$ ratio). In addition, RCD is known to cause multiple secondary defects in numerous additional pathways including, for example, the pyrimidine biosynthesis pathway (King and Attardi, 1989). Ideally, a cure for RCDs would correct the primary genetic lesion in the patient's mitochondria. However, such a treatment would require gene therapy or protein replacement therapy to target a majority of patient tissues and cells. Moreover, such "biologic" therapy would need to be developed specifically for each of the 150 different genetic forms of mitochondrial disease, each of which is very rare. To find more generic solutions to address RCDs we are exploring the concept of alleviating the reductive stress component.

Although ATP (i.e., energy) insufficiency is classically considered to be a major cause of RCD-related diseases, the present study investigates the role of reductive stress (increased NADH/NAD$^+$) as an alternative contributor to pathogenesis. There are several reasons to think that reductive stress is an important disease-causing mechanism: (a) Patients with RCD are able to switch to glycolysis as an alternative source of cellular energy to buffer against deficiencies in ATP (von Kleist-Retzow et al., 2007). (b) Reductive stress itself can inhibit glycolysis because re-oxidation of NADH is known to activate this pathway (Martinus et al., 1993). Therefore, reductive stress can ultimately contribute to energetic stress by preventing even glycolytic ATP generation. (c) Reductive stress blocks many biosynthetic pathways, e.g., pyrimidine biosynthesis, and therefore can block cell proliferation (Khutornenko et al., 2010; Morais et al., 1982). As previously demonstrated, intracellular expression of water-forming NADH oxidases can alleviate reductive stress to enable cells to proliferate even when their respiratory chain is chemically lesioned (Titov et al., 2016).

Figure 1A:
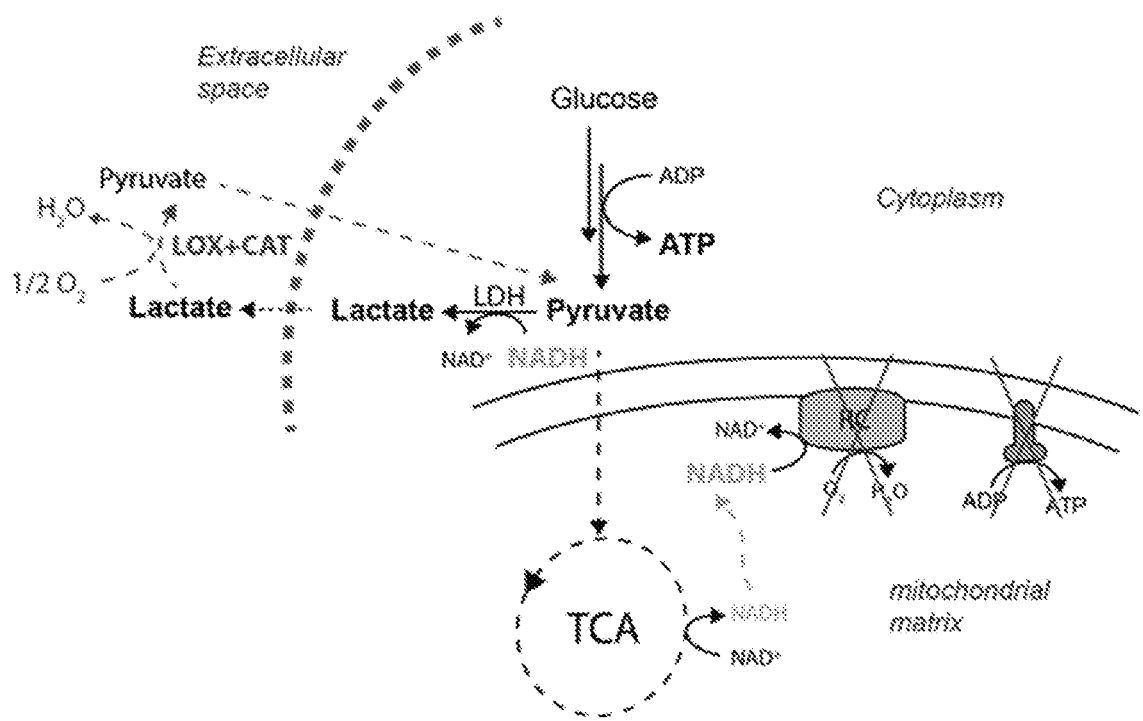
FIGS. 1A-B. Illustrative schematics of: (A) Proposed scheme for alleviating reductive stress. The majority of cytoplasmic NADH is normally oxidized by the mitochondrial respiratory chain to produce ATP in oxidative phosphorylation. However, with respiratory chain dysfunction, cells rely on glycolysis for their ATP supply and oxidize their NADH in the LDH reaction that produces lactate from pyruvate. Lactate then diffuses into the bloodstream (extracellular space). We propose to convert the extracellular lactate back to pyruvate through the action of lactate oxidase (LOX) and catalase (CAT). This extracellular pyruvate then will participate in the LDH reaction to further oxidize NADH. (B) The lactate oxidase reaction converts one mole of lactate and one mole of oxygen into one mole of pyruvate and produces one mole of unwanted and toxic byproduct hydrogen peroxide ($H_2O_2$). Catalase, a second enzyme, will detoxify $H_2O_2$ by converting it into water and oxygen. The overall reaction of the combination of these two enzymes is conversion of two moles lactate to two moles of pyruvate, while consuming one mole of oxygen to produce two moles of water.

The present methods relate to introduction of extracellular enzymes, i.e., LOX and CAT or LOXCAT, a single polypeptide containing LOX and CAT, both of which indirectly alleviate intracellular reductive stress. This strategy will not correct the underlying lesion of the mitochondria but will rather enzymatically manipulate the extracellular lactate/pyruvate ratio to secondarily regulate the intracellular NADH/NAD$^+$ ratio. Lactate is produced by the reduction of pyruvate by the cytoplasmic enzyme lactate dehydrogenase (LDH). This reaction requires oxidation of a molecule of NADH to NAD$^+$ (FIG. 1A). Both lactate and pyruvate are transported across the plasma membrane by monocarboxylate transporters (MCTs) (Halestrap, 2012). In the absence of mitochondrially produced ATP in RCD, the cell mostly depends on glycolysis to meet its energy needs (Vafai et al., 2016). Glycolysis requires a constant supply of NAD$^+$, so cells under these conditions further drive the LDH reaction in the direction of NADH oxidation, ultimately producing excessive amounts of lactate. In fact, blood lactate levels are often elevated in mitochondrial diseases (Shaham et al., 2010). Classically, the extracellular lactate/pyruvate ratio is used as a proxy for the intracellular NADH/NAD$^+$ ratio (Williamson et al., 1967). Moreover, it has also been shown that clamping extracellular lactate/pyruvate ratios by adding these two chemicals in excess in the media can impact intracellular NADH/NAD$^+$ ratios (Bucher et al., 1972; Hung et al., 2011).

Figure 1B:
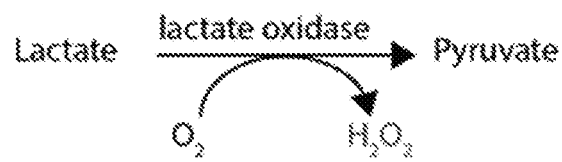
Figure 1B:
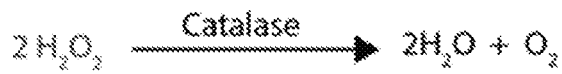
Figure 1B:
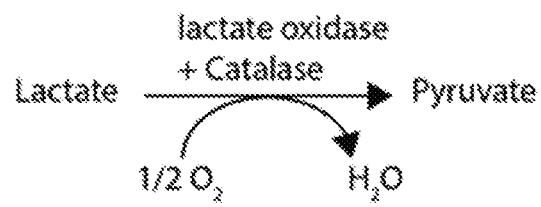

The present methods are based on enzymatically converting extracellular lactate produced by glycolysis back to pyruvate, which can then enter the cell to participate in the LDH reaction to allow further oxidation of NADH. The end product of such pyruvate regeneration is oxidation of one mole of NADH per mole of lactate oxidized extracellularly (FIG. 1A). The present methods use lactate oxidase, a bacterial enzyme that converts lactate and oxygen to pyruvate and hydrogen peroxide (FIG. 1B). A second enzyme, catalase, is used to convert hydrogen peroxide, a potentially toxic molecule, into water and oxygen (FIG. 1B). The overall effect of extracellular LOX and CAT combined with endogenous LDH thus is to transfer electrons from NADH to O$_2$ to produce water, a function that the mitochondrial respiratory chain performs in healthy cells.

Enzymatic manipulation of an extracellular metabolite released by the cell to affect the redox state of the cell has a number of therapeutic applications as the NADH/NAD$^+$ ratio is elevated in numerous human diseases, including a spectrum of mitochondrial diseases (Thompson Legault et al., 2015) and diabetes (Williamson et al., 1993). This strategy can be used extracellularly, so it should not require any intracellular modification or targeting. The methods can include administering the enzyme system (in an appropriate formulation), e.g., intravenously, to effectively convert extracellular lactate to pyruvate to restore cellular redox homeostasis. Also, since pyruvate and lactate both cross the blood brain barrier (Boumezbeur et al., 2010; Cremer et al., 1979), the methods can also be used to reduce reductive stress in CNS tissue. There is precedent for the use of bacterial enzymes in blood to treat human diseases; for example, asparaginase that depletes blood asparagine, an essential amino acid for tumor cells but not for healthy cells, is used clinically to treat acute lymphoblastic leukemia (Muller and Boos, 1998; Mashburn and Wriston, Arch Biochem Biophys. 1964 May; 105:450-2; ).

Previously, other approaches have been used to modulate the intracellular NADH/NAD$^+$ ratio. An enzyme-based approach has been described wherein expression of enzyme NADH oxidase (NOX) from *Lactobacillus brevis* (named LbNOX) in mammalian cells compartment-specifically reduced either the cytosolic or the mitochondrial NADH/NAD$^+$ ratio in vitro (Titov et al., 2016). The LbNOX enzyme perturbs the NADH/NAD$^+$ ratio by directly converting NADH to NAD$^+$ while consuming one mole of oxygen per mole of NADH and producing water as a byproduct. However, this strategy is limited in its therapeutic applicability as it requires gene therapy to introduce LbNOX in each of the patient tissues because NAD$^+$ and NADH are not cell permeable. Similarly, small molecule substrates of NQO1, an NAD(P)H dependent oxidoreductase, have been used to oxidize intracellular NADH. One such molecule is natural product β-lapachone that is activated by NQO1 to an unstable hydroquinone that rapidly undergoes a two-step oxidation back to the parent compound, continuing a futile redox cycle (oxidation of NAD(P)H) and generating toxic superoxide in this process (Hwang et al., 2009; Pink et al., 2000; Zhao et al., 2015). Unfortunately, β-lapachone has low solubility and in vivo half-life (about 20 minutes) (Blanco et al., 2010). Similarly, Zhao et al discovered cancer cell specific cytotoxic small molecule KP372-1 that decreases the NADH/NAD$^+$ ratio via NQO1 (Zhao et al., 2015). Both β-lapachone and KP372-1 are known to induce severe oxidative stress by producing superoxide and hydrogen peroxide. Moreover, K372-1 was originally reported as an inhibitor kinase Akt (Koul et al., 2006), suggesting this molecule has multiple targets in the cell. The present compositions and methods circumvent the shortcomings of LbNOX, β-lapachone and KP372-1, as (a) NADH/NAD$^+$ is modulated extracellularly and does not require any intracellular genetic manipulation, (b) the enzymes have more specific effects than small molecules, and (c) it will not generate toxic reactive oxygen species.

LOX+CAT or LOXCAT

The present methods include the administration of a composition comprising lactate oxidase (LOX) and Catalase (CAT), preferably in a 1:1 molar ratio. In some embodiments, the methods include the administration of a composition comprising a fusion polypeptide comprising both LOX and CAT, e.g., LOXCAT as described herein.

Lactate Oxidase (LOX)

LOX sequences that can be used in the present methods include those that are orthologs, homologs or show at least 80% identity to the full length of SEQ ID NO:6, and that can convert lactate and oxygen to pyruvate and hydrogen peroxide. In some embodiments, the LOX sequences are at least 85%, 90%, 95%, or 99% identical to the full length of SEQ ID NO:6, e.g., have up to 41, 35, 30, 25, 20, 15, 10, 5, or 1 amino acid substitutions, deletions, or insertions. Other exemplary LOX sequences include L-LOX from *Pediococcus acidilactici* (GeneBank: APR28621.1), *Streptococcus pneumoniae* (GenBank: AFS42797.1) and *Lactobacillus plantarum* (GenBank: ATI72793.1). Alternatively, a D-lactate oxidase from gram negative soil bacterium KY6 (Xu et al., et al. Appl Biochem Biotechnol (1996) 56: 277) or from *Zymomonas mobilis* (Kalnenieks et al., 1998) could be used.

Catalase (CAT)

CAT sequences that can be used in the present methods include those that are orthologs, homologs or show at least 80% identity to SEQ ID NO:4 and can convert hydrogen peroxide, a potentially toxic molecule, into water and oxygen. In some embodiments, the CAT sequences are at least 85%, 90%, 95%, or 99% identical to the full length of SEQ ID NO:6, e.g., have up to 100, 90, 80, 70, 60, 50, 40, 35, 30, 25, 20, 15, 10, 5, or 1 amino acid substitutions, deletions, or insertions. Other exemplary CAT sequences include catalase from *Homo sapiens* (NCBI Reference Sequence: NP_001743.1), *Mus musculus* (NCBI Reference Sequence: NP_033934.2), and *Caenorhabditis elegans* (NCBI Reference Sequence: NP_001293540.1).

Sequence Identity

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can determined using the Needleman and Wunsch ((1970) J. Mol. Biol. 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

LOXCAT

In some embodiments, a LOXCAT fusion protein is used, e.g., a fusion protein comprising a LOX sequence and a CAT sequence as described herein, with an optional linker, and optionally one or more additional sequences between the LOX and CAT or at the N or C terminus.

In preferred embodiments, a linker of from 1-50 amino acids, e.g., a flexible linker, is present between the LOX and CAT. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:7) or GGGGS (SEQ ID NO:8), e.g., two, three, four, or more repeats of the GGGS (SEQ ID NO:7) or GGGGS (SEQ ID NO:8) unit. Other linker sequences can also be used. In some embodiments, a linker comprising a 20-amino acid L-linker (ASGAGGSEGGGSEGGTSGAT (SEQ ID NO:5)) is used.

In some embodiments, the variants include a moiety that has a high affinity for a ligand, for example GST, FLAG or hexahistidine sequences. Such affinity tags can facilitate the purification of recombinant variant proteins.

In some embodiments, the fusion protein comprises one or more enzyme cleavage sites, e.g., thrombin LVPRGS (SEQ ID NO:2) or enterokinase/enteropeptidase DDDDK (SEQ ID NO:3) cleavage sites. Other cleavage sites can also be used, e.g., Human Rhinovirus 3C Protease; Factor Xa (FXa); or Tobacco Etch Virus Protease (TEV). These cleavage sites can be used, e.g., to recover the protein after affinity purification. See, e.g., Waugh et al., Protein Expr Purif. 2011 December; 80(2): 283-293.

An exemplary LOXCAT sequence was designed by combining a catalase from *E. coli* at the N-terminus and *Aerococcus viridans* lactate oxidase (LOX) at the C-terminus; the other orientation (wherein the LOX is at the N-terminus and the catalase is at the C-terminus) can also be used. These two polypeptides were fused together by a 20-amino acid linker, known as the L-20 linker.

Exemplary Amino Acid Sequence of an Engineered LOX-CAT Fusion Polypeptide:

(SEQ ID NO: 1)
M*HHHHHH*SSGLVPRGSGMKETAAAKFERQHMDSPDLGTDDDDKAMADIGSE

FELSQHNEKNPHQHQSPLHDSSEAKPGMDSLAPEDGSHRPAAEPTPPGAQP

TAPGSLKAPDTRNEKLNSLEDVRKGSENYALTTNQGVRIADDQNSLRAGSR

GPTLLEDFILREKITHFDHERIPERIVHARGSAAHGYFQPYKSLSDITKAD

FLSDPNKITPVFVRFSTVQGGAGSADTVRDIRGFATKFYTEEGIFDLVGNN

TPIFFIQDAHKFPDFVHAVKPEPHWAIPQGQSAHDTFWDYVSLQPETLHNV

MWAMSDRGIPRSYRTMEGFGIHTFRLINAEGKATFVRFHWKPLAGKASLVW

DEAQKLTGRDPDFHRRELWEAIEAGDFPEYELGFQLIPEEDEFKFDFDLLD

-continued

```
PTKLIPEELVPVQRVGKMVLNRNPDNFFAENEQAAFHPGHIVPGLDFTNDP

LLQGRLFSYTDTQISRLGGPNFHEIPINRPTCPYHNFQRDGMHRMGIDTNP

ANYEPNSINDNWPRETPPGPKRGGFESYQERVEGNKVRERSPSFGEYYSHP

RLFWLSQTPFEQRHIVDGFSFELSKVVRPYIRERVVDQLAHIDLTLAQAVA

KNLGIELTDDQLNITPPPDVNGLKKDPSLSLYAIPDGDVKGRVVAILLNDE

VRSADLLAILKALKAKGVHAKLLYSRMGEVTADDGTVLPIAATFAGAPSLT

VDAVIVPCGNIADIADNGDANYYLMEAYKHLKPIALAGDARKFKATIKIAD

QGEEGIVEADSADGSFMDELLTLMAAHRVWSRIPKIDKIPAASGAGGSEGG

GSEGGTSGATNNNDIEYNAPSEIKYIDVVNTYDLEEEASKVVPHGGFNYIA

GASGDEWTKRANDRAWKHKLLYPRLAQDVEAPDTSTEILGHKIKAPFIMAP

IAAHGLAHTTKEAGTARAVSEFGTIMSISAYSGATFEEISEGLNGGPRWFQ

IYMAKDDQQNRDILDEAKSDGATAIILTADSTVSGNRDRDVKNKFVYPFGM

PIVQRYLRGTAEGMSLNNIYGASKQKISPRDIEEIAGHSGLPVFVKGIQHP

EDADMAIKRGASGIWVSNHGARQLYEAPGSFDTLPAIAERVNKRVPIVFDS

GVRRGEHVAKALASGADVVALGRPVLFGLALGGWQGAYSVLDYFQKDLTRV

MQLTGSQNVEDLKGLDLFDNPYGYEY

His6-tag - HHHHHH

Thrombin cleavage site -
                                            (SEQ ID NO: 2)
LVPRGS Enterokinase cleavage site -
                                            (SEQ ID NO: 3)
DDDDK Catalase (HPII) from E. coli -
                                            (SEQ ID NO: 4)
SQHNEKNPHQHQSPLHDSSEAKPGMDSLAPEDGSHRPAAEPTPPGAQPTAP

GSLKAPDTRNEKLNSLEDVRKGSENYALTTNQGVRIADDQNSLRAGSRGPT

LLEDFILREKITHFDHERIPERIVHARGSAAHGYFQPYKSLSDITKADFLS

DPNKITPVFVRFSTVQGGAGSADTVRDIRGFATKFYTEEGIFDLVGNNTPI

FFIQDAHKFPDFVHAVKPEPHWAIPGQSAHDTFWDYVSLQPETLHNVMWA

MSDRGIPRSYRTMEGFGIHTFRLINAEGKATFVRFHWKPLAGKASLVWDEA

QKLTGRDPDFHRRELWEAIEAGDFPEYELGFQLIPEEDEFKFDFDLLDPIK

LIPEELVPVQRVGKMVLNRNPDNFFAENEQAAFHPGHIVPGLDFTNDPLLQ

GRLFSYTDTQISRLGGPNFHEIPINRPTCPYHNFQRDGMHRMGIDTNPANY

EPNSINDNWPRETPPGPKRGGFESYQERVEGNKVRERSPSFGEYYSHPRLF

WLSQTPFEQRHIVDGFSFELSKVVRPYIRERVVDQLAHIDLTLAQAVAKNL

GIELTDDQLNITPPPDVNGLKKDPSLSLYAIPDGDVKGRVVAILLNDEVRS

ADLLAILKALKAKGVHAKLLYSRMGEVTADDGTVLPIAATFAGAPSLTVDA

VIVPCGNIADIADNGDANYYLMEAYKHLKPIALAGDARKFKATIKIADQGE

EGIVEADSADGSFMDELLTLMAAHRVWSRIPKIDKIPA

L20 linker -
                                            (SEQ ID NO: 5)
ASGAGGSEGGGSEGGTSGAT

Lactate oxidase (LOX) from Aerococcus viridans -
                                            (SEQ ID NO: 6)
NNNDIEYNAPSEIKYIDVVNTYDLEEEASKVVPHGGFNYIAGASGDEWTKR

ANDRAWKHKLLYPRLAQDVEAPDTSTEILGHKIKAPFIMAPIAAHGLAHTT

KEAGTARAVSEFGTIMSISAYSGATFEEISEGLNGGPRWFQIYMAKDDQQN

RDILDEAKSDGATAIILTADSTVSGNRDRDVKNKFVYPFGMPIVQRYLRGT

AEGMSLNNIYGASKQKISPRDIEEIAGHSGLPVFVKGIQHPEDADMAIKRG

ASGIWVSNHGARQLY
```

Albumin Binding Peptide (ABP) Containing LOXCAT

In some embodiments, the fusion protein comprises an albumin binding peptide. Albumin is the most abundant protein in the bloodstream (~45%) with a half-life of 19 days. Human serum albumin (HAS) has been studied as a drug carrier for various clinical applications. It has recently also been used to confer higher in vivo stability to biologics. An Albumin Binding Peptide (ABP) (sequence DICL-PRWGCLEWED (SEQ ID NO:9))-tagged proteins have shown improved stability in the bloodstream (J Biol Chem. 2002 Sep. 20; 277(38):35035-43, PLoS ONE 9, e106422 (2014) and Protein Engineering, Design & Selection vol. 17 no. 10 pp. 731-739, 2004). Attachment of this albumin binding peptide sequence, at either the N- or the C-terminal of the fusion proteins, can be used to improve serum stability of LOXCAT. In some embodiments, the ABP is included at the N-terminus of the LOXCAT fusion protein.

Methods of Delivering LOX+CAT or LOXCAT to Patients

Any of several delivery modalities can be used for the LOXCAT-based therapies described herein. For example, the fused LOXCAT can be delivered using—(a) red blood cell (RBC) encapsulation (e.g., as described in Muzykantov, 2010), or (b) enzyme attachment to RBC outer surface (e.g., as described in Shi et al., 2014), or (c) engineered bone marrow transplant, or (d) direct injection of appropriately formulated purified enzyme (e.g., as described in Pisal et al., 2010).

A. RBC Encapsulation.

In the RBC encapsulation approach, a purified enzyme is loaded into red blood cells by using hypotonic dialysis (Alpar and Lewis, 1985). Such encapsulated enzymes show enhanced half-life in the circulation as well as reduces immune reactions compared to direct injection of formulated enzymes. Enzymes inside RBC usually remain active for days unlike in other strategies, which allows lower dosage of the biologic drug (Muzykantov, 2010). RBC encapsulation has been used to deplete blood metabolites using non-human enzymes like urate oxidase from Aspergillus flavus to detoxify excessive uric acid (Ihler et al., 1975) and asparaginase from E. coli to remove L-asparagine from blood to kill cancer cells (Alpar and Lewis, 1985; Domenech et al., 2011; Updike et al., 1976; Agrawal et al., Protein & Peptide Letters, 2013, 20, 392-402). Previously, lactate oxidase has been successfully encapsulated in RBCs. Garin et al RBC encapsulated a mixture of lactate monooxygenase (LMO) and lactate oxidase (LOX) at a ratio of 20:1 with the aim of depleting excessive lactate in hyperlactataemia (Garin et al., 1995). The enzyme LMO catalyzes the conversion of one mole of lactate into one mole of acetate while consuming one mole of oxygen and producing one mole of $CO_2$ and one mole of $H_2O$ as byproducts. They showed that this combination of LMO and LOX could catabolize lactate in the concentration range of 1-30 mM in vitro. However, in vivo attempts were not successful, possible because of the high oxygen capacity of the enzymes (both enzymes consume one mole oxygen per mole of substrate) and high lactate metabolism. The Garin et al. method converted lactate into a mixture of pyruvate, acetate, $H_2O$, $H_2O_2$ and $CO_2$. Increased blood concentrations of $H_2O_2$ could lead to oxidative damage and increased $CO_2$ concentrations could lead to blood pH imbalance.

In contrast, the present methods, including the LOXCAT fusion protein, produce pyruvate and water from lactate and oxygen. LOXCAT does not produce any toxic $H_2O_2$ byproduct and consumes only one mole of oxygen per two moles of lactate. Garin et al. suggests that RBC encapsulation of LOX is possible, and the enzyme remains active. Similarly, Hamarat Baysal et al. encapsulated catalase and PEGylated-catalase inside RBCs to detoxify $H_2O_2$ (Hamarat Baysal and Uslan, 2001), indicating that a functional catalase could also be entrapped in RBCs. Furthermore, RBCs express monocarboxylate transporters and are known to take up lactate (Smith et al., 1997), so enveloping the present enzymes should not impede their ability to process circulating lactate.

In some embodiments, the LOXCAT fusion protein is encapsulated using the membrane-translocating low molecular weight protamine (LMWP), e.g., as described in Kwon et al., Journal of Controlled Release 139 (2009) 182-189; thus included herein are LMWP-LOXCAT conjugates.

B. Enzyme Attachment to the Outer Surface of RBCs

Another delivery option is to use engineered RBCs to attach LOXCAT to their outer surface and then introduce these modified RBCs into a subject. RBCs have been engineered to express membrane protein Kell with a C-terminal LPXTG-tag that is amenable to the sortase reaction (Shi et al., 2014). The sortase reaction allows attachment of different enzymes to these recombinant Kell expressing RBCs' outer surface as long as they contain three N-terminal glycine residues. Such RBC attachment could help the enzyme evade the immune system and confer improved proteolytic stability. The addition of three glycine residues at the N-terminus of LOX+CAT, or LOXCAT can be used for attachment to RBCs; thus included herein are GGG-LOX-CAT fusion proteins.

C. Engineered Bone Marrow

Another similar strategy to deliver LOX+CAT or LOX-CAT is to use engineered bone marrow. In this approach, initially subject-derived bone marrow is engineered with the target enzyme gene (LOX+CAT or LOXCAT), e.g., using adeno-associated virus (AAV). The engineered bone marrow is then transplanted back into the subject so that a population of the subject's matured blood cells carry the target enzyme. This strategy may have the same advantages as RBC encapsulation.

D. Parenteral Administration

The direct administration approach is the most common strategy to deliver biologics into the bloodstream. Pharmaceutical compositions are typically formulated to be compatible with its intended route of administration. Examples of routes of administration include parenteral, e.g., intravenous, intramuscular, and subcutaneous.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811. In some embodiments, the enzyme is formulated with PEGylation (Pisal et al., 2010).

The pharmaceutical compositions can be included in a container, pack, or dispenser together with instructions for administration.

Methods of Treatment

The methods described herein include methods for the treatment of disorders associated with respiratory chain dysfunction (RCD). In some embodiments, the disorder is lactic acidosis (e.g., in sepsis); D-lactic acid toxicity (e.g., in Short bowel syndrome); a mitochondrial disorder; cancer; ischemia-reperfusion injury; cardiac arrest; or type 2 diabetes. Generally, the methods include administering a therapeutically effective amount of LOXCAT or LOX+CAT as described herein, to a subject who is in need of, or who has been determined to be in need of, such treatment.

As used in this context, to "treat" means to ameliorate at least one symptom of the disorder associated with RCD. Often, RCD results in excessive amounts of lactate buildup; thus, a treatment can result in a reduction in lactate levels, an increase in blood pyruvate levels below a threshold, and/or a decrease in blood lactate/pyruvate ratio. The increase or decrease can be by a desired amount or by an amount sufficient to bring the levels or ration above or below a threshold. Administration of a therapeutically effective amount of a compound described herein for the treatment of a condition associated with RCD will result in decreased reduced blood lactate levels.

The methods can include measuring one or both of lactate and pyruvate, and optionally calculating a lactate/pyruvate ratio. A number of methods are known in the art for measuring levels of lactate and/or pyruvate in the blood of a subject, including e.g., enzymatic detection, spectroscopy, NMR, mass spectrometry (MS), gas chromatography (GC), liquid chromatography (LC), and combinations thereof, e.g., GC-MS, LC-MS, LC-MS/MS. Normal ranges for blood pyruvate levels can vary depending on the assay used, but are usually 50-100 µM, both in humans and in mice (see, e.g., Hui et al., Nature. 2017 Nov. 2; 551(7678):115-118 and Human Metabolome Database (HMDB, online at hmdb.ca/metabolites/HMDB0000243). LOXCAT injected in mouse blood increased pyruvate concentrations to over 500 µM in 15 min. Normal ranges for blood lactate levels can vary depending on the assay used, but are about 0.3-2.0 mmol/L, with elevations about 2.1 mM seen as a potential marker of mitochondrial disease (Haas et al., Mol Genet Metab. 2008 May; 94(1):16-37). Pyruvate, in the presence of excess NADH, H+, and lactic dehydrogenase, is reduced to lactate. The reaction is stoichiometric; the decrease in absorbance at 340 nm is directly proportional to the concentration of pyruvate (Standard Methods of Clinical Chemistry, 1979; 6:245-259; Huckabee, J Clin Invest 1958; 37:244-254). See also Foster et al., Clin Chem. 1978 September; 24(9):1568-72; Debray et al., Clin Chem. 2007 May; 53(5):916-21; Chariot et al., Arthritis & Rheumatism 1994; 37(4):583-586.

Altering cytoplasmic redox balance by reducing blood lactate load can conceivably be of great therapeutic utility in a variety of disease and conditions, including the following.

Lactic acidosis: This condition is defined by a blood lactate concentration>4-5 mM and a pH<7.35 and could stem from various underlying diseases, including mitochondrial dysfunction, sepsis (Bakker et al., 1991), etc. Typically, normal blood lactate concentration in unstressed patients is 0.5-1 mmol/L. Patients with critical illness can be considered to have normal lactate concentrations of less than 2 mmol/L. Hyperlactatemia is defined as a mild to moderate persistent increase in blood lactate concentration (2-4 mmol/L) without metabolic acidosis, whereas lactic acidosis is characterized by persistently increased blood lactate levels (usually >4-5 mmol/L) in association with metabolic acidosis. See, e.g., Cohen and Woods, *Clinical and Biochemical Aspects of Lactic Acidosis*. London, United Kingdom: Blackwell Scientific Publications; 1976; Mizock and Falk, Crit Care Med. 1992 Jan. 20(1):80-93; and Seheult et al., Clin Chem Lab Med. 2017 Mar. 1. 55 (3):322-33.

Figure 8:
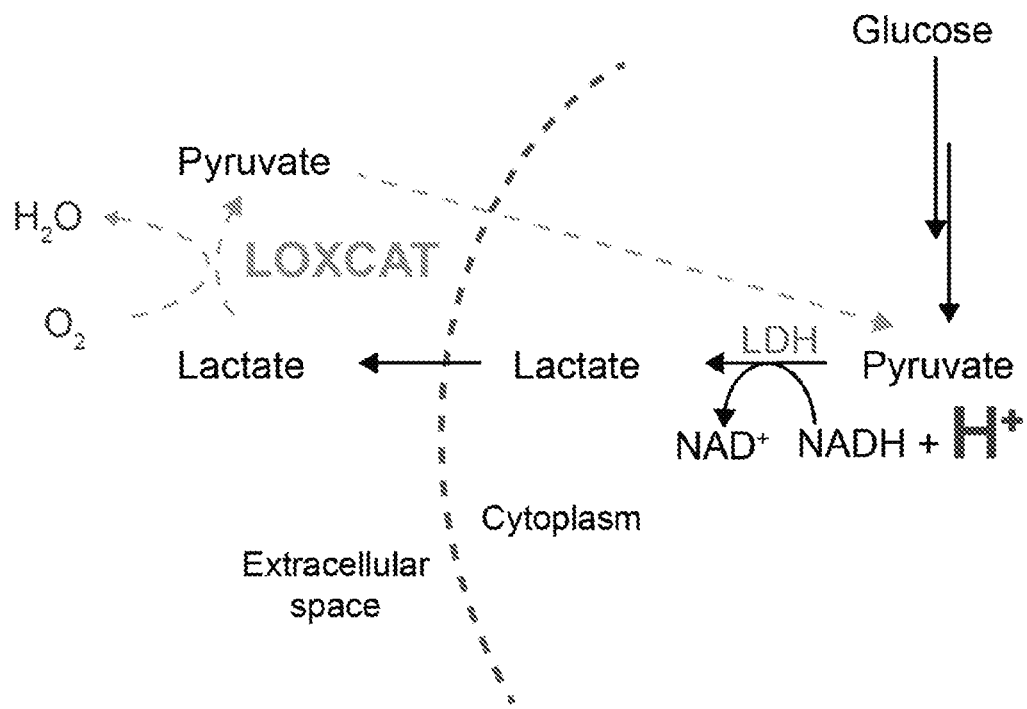
FIG. 8. LOXCAT could reduce lactic acidosis. Driving LDH reaction more towards NADH oxidation could reduce lactic acidosis by increasing blood pH, as the LDH reaction in the direction of NADH oxidation reduces the cytoplasmic proton concentrations. Proton that contributes to cytoplasmic acidity is shown in large bold gray font.

Currently, there is no good way to treat or manage lactic acidosis in the clinic. Ideally, one would want to correct the underlying cause that leads to lactic acidosis, but for episodes of acute lactic acidosis a fast acting therapy that could both reduce blood lactate and acidity could save lives. LOXCAT/LOX+CAT could be used to manage such acute lactic acidosis episodes, as it will both reduce blood lactate levels and push the LDH reaction in the direction of oxidation of NADH reducing the number of protons in the cytosol (FIG. 8). The NADH oxidation reaction accompanies reduction of a proton in the media, which will ultimately increase pH. Either increased pyruvate concentrations or depletion of lactate or both could drive the LDH reaction in the direction of NADH oxidation. It has previously been shown in mice that pushing the LDH reaction in the direction of NADH oxidation could alleviate lactic acidosis (Acharya et al., 2014). So, the same results are expected with LOXCAT/LOX+CAT because LOXCAT/LOX+CAT induces oxidation of NADH, presumably by the driving LDH reaction forward. Thus, LOXCAT/LOX+CAT can be used as therapy in managing lactic acidosis in the clinic.

Diabetes: Aberrant cytoplasmic $NADH/NAD^+$ ratios are thought to underlie much of diabetes pathogenesis (Williamson et al., 1993; Yan, J Diabetes Res. 2014; 2014:137919). Therefore, LOXCAT/LOX+CAT administration could be beneficial in treating subjects with diabetes, or in reducing the risk of developing diabetes, e.g., in subjects who are chronically overnutrited, have a high BMI (e.g., BMI of 25 or higher, or 29 or higher), or who have chronic hyperglycemia (e.g., blood glucose levels above 100 mg/dL lasting for weeks or months) but who do not yet have full blown diabetes.

Cancer/Cancer immunotherapy: Lactate has been reported as an immune-suppressor. According to current hypothesis, lactate released by the cancer cells blind effector T-cells from attacking and killing cancer cells (Brand et al., 2016; Fischer et al., 2007). This could be one reason why cancer immunotherapy fails in some instances, as currently available immunotherapies do not take care of the excessive lactate concentrations in the cancer microenvironment. Depleting lactate from the cancer microenvironment could improve cancer immunotherapy. In this scenario, LOXCAT/LOX+CAT could be used alone or in conjunction with currently available immunotherapy for improved outcomes. Also, cancer cells show higher $NADH/NAD^+$ ratios and certain anticancer drugs specifically kill cancer cells by lowering this ratio (Zhao et al., 2015). So, LOXCAT/LOX+CAT could also be effective as an anticancer therapeutic because of its ability to lower the $NADH/NAD^+$ ratio in cells.

D-lactic acid toxicity:Lactic acid has two stereoisomers: L- and D-lactic acids. Both D- and L-lactate could be produced from pyruvate, which is does not have stereoisomers, by the corresponding LDH reaction (L-LDH produces L-lactate and D-LDH produces D-lactate). Conversely, both L- and D-lactates could be converted into pyruvate, by using the corresponding LDH or LOX. L-lactate is the predominant form in humans and animals because they possess only L-LDH, whereas D-lactic acid is produced mostly by bacteria because bacteria have D-LDH. However, now it has come to light that humans could also produce D-lactic acid in a pathway known as the glyoxalase system, in which highly toxic glycolytic byproduct methylglyoxal is converted into less toxic D-lactate by the action of the enzymes GLO1 and GLO2. Increased concentration of D-lactate, under certain conditions, has been reported to be toxic to humans because it could inhibit some important metabolic pathways (Ling et al., 2012). This D-lactate could either be human cell-derived or human gut microbiota-derived. Short bowel syndrome, for example, manifests in severe D-lactic acidosis (Kowlgi and Chhabra, 2015). Engineered LOXCAT/LOX+CAT can be used to deplete toxic amounts of D-lactate in D-lactic acidosis. Although the exemplary version of LOXCAT described contains L-LOX, which converts L-lactate into pyruvate, L-LOX can be replaced with D-LOX in LOXCAT to detoxify D-lactate in blood. D-LOX is naturally present in bacteria *Zymomonas mobilis* (Kalnenieks et al., 1998). This proposed D-LOXCAT (or D-LOX+CAT) should be able to both degrade toxic D-lactate and reduce acidosis by oxidizing more NADH in the LDH reaction because oxidation of D-lactate will produce pyruvate, just as in the case of L-lactate.

Mitochondrial Disease. More than 150 distinct genetic mitochondrial syndromes have been defined; many are associated with RCD (see, e.g., Vafai and Mootha, 2012; Munnich et al., in *Scriver's Online Metabolic and Molecular Basis of Inherited Disease* (eds Valle, D. et al.) Ch. 99, dx.doi.org/10.1036/ommbid.127 (McGraw-Hill, 2006); Shoffner, in *Scriver's Online Metabolic and Molecular Basis of Inherited Disease* (eds Valle, D. et al.) Ch. 104, dx.doi.org/10.1036/ommbid.127 (McGraw-Hill, 2006)), including Leigh Syndrome (Legault et al., 2015, Cell Reports 13, 981-989), Mitochondrial Myopathy, Encephalopathy, Lactic acidosis and Stroke-like syndrome (MELAS) and Leber's hereditary optical neuropathy (LEON). All these diseases manifest in an imbalance of [NADH]/[NAD+] with increased blood lactate (e.g., blood plasma concentration remains above an approximate reference range of 0.5-1.5 mmol/L). Since LOXCAT could reduce both the [Lactate]/[Pyruvate] and the [NADH]/[NAD$^+$], it could be used as a therapeutic for these disorders.

Aging and neurodegenerative disease. NAD$^+$ insufficiency has been postulated to be a major cause of aging (Haigis and Guarente, 2006), and altered NADH/NAD$^+$ ratios have been proposed as a mechanism by which caloric restriction extends lifespan (Lin et al., 2004). Also, it has been shown that brain lactate concentrations increase with aging (Ross et al., 2010) and pyruvate supplementation is beneficial in aging and Alzheimer's disease mouse models (Koivisto et al., 2016). Together, LOXCAT/LOX+CAT is a potential therapeutic in age-related and neurodegenerative disorders, reducing or delaying symptoms of aging.

Ischemia-Reperfusion Injury. Ischemia increases lactate (Chouchani et al., Nature. 2014 Nov 20; 515(7527):431-435; Kintu-Luwaga et al., Int J Emerg Med. 2013; 6(1):44 (intestinal ischemia)) and reperfusion very acutely produces hydrogen peroxide (Chouchani et al., Nature. 2014 Nov. 20; 515(7527):431-435 and Chouchani et al., Cell Metab. 2016 Feb. 9; 23(2):254-63). LOXCAT in blood can be used to acutely reduce lactate and increase pyruvate during the reperfusion phase. Also, LOXCAT can be used to acutely quench hydrogen peroxide produced during repercussion, because it has catalase and pyruvate non-enzymatically reacts with hydrogen peroxide to make water. Pyruvate has already been shown to be beneficial in ischemia-reperfusion (Ryou et al., Stroke. 2012 April; 43(4):1101-7 (brain) and Cicalese et al., Am J Surg. 1996 January; 171(1):97-100; discussion 100-1 (intestine)).

Cardiac Arrest. Higher blood lactate in this indication has been clinically correlated with higher mortality rate (Donnino et al., Crit Care Med 42, 1804-181 (2014)) and pyruvate infusion in animal models has shown to improve metabolic and neurological functions (Sharma et al., Resuscitation 76, 108-119 (2008); Sharma et al., Resuscitation 66, 71-81 (2005)). Also, therapeutic hypothermia, which is the only available treatment for post cardiac arrest syndrome, has shown to reduce the circulating lactate/pyruvate ratio (Nordmark et al., Resuscitation 80, 573-579 (2009)). Post cardiac arrest syndrome (PCAS) refers to the pathophysiological consequences of return of spontaneous circulation (ROSC) after successful cardiopulmonary resuscitation (CPR), usually manifests in severe brain injury and cardiovascular instability. Only 10-20% of patients that achieve successful CPR survive until hospital discharge and brain injury accounts for two-thirds of deaths after ROSC. Moreover, cerebral mitochondrial dysfunction has been implicated in brain injury during PCAS and mitochondrial DNA copy number has been linked to risks of cardiac failure (Jiang et al., Biomed Res Int 2014, 192769 (2014); Gazmuri and Radhakrishnan, Crit Care Clin 28, 245-270 (2012); Zhang et al., Eur Heart J 38, 3443-3448 (2017)). Out of hospital cardiac arrest kills 250,000 Americans each year and only approximately 6% of out of hospital cardiac arrest patients survive worldwide. Except for hypothermia, which is an experimental therapeutic for PCAS, there is no other treatment available for this indication. However, hypothermia treatment requires immediate access to a facility equipped with this labor-intensive process that usually last for over 24 h. On the other hand, as shown herein, LOXCAT treatment shows similar survival rates as hypothermia and requires just a single shot of it before performing CPR. Moreover, LOXCAT could be made available to places where immediate access to hypothermia treatment is limited. Therefore, LOXCAT could serve as a more accessible and easy to administer potential drug for post cardiac arrest syndrome.

Traumatic Brain injury (TBI). TBI is caused by violent insult to the brain that leads to physical and psychological defects. Currently there is no therapy available for TBI. Clinically, elevated cerebral extracellular lactate (Carpenter, et al., Front Neurosci 9, 112 (2015)) and lactate/pyruvate ratio correlate with worse outcome (Timofeev et al., Brain: a journal of neurology 134:484-494 (2011)). Pyruvate treatment has been shown to improve cerebral metabolism and reduce neuronal cell death in animal models (Moro and Sutton, Exp Neurol 225:391-401 (2010)). TBI also leads to mitochondrial dysfunction (Xiong et al., J Neurotrauma 14:23-34 (1997)). Since both lactate and pyruvate cross the blood-brain barrier within minutes (Knudsen et al., J Cereb Blood Flow Metab 11, 581-586 (1991); Miller and Oldendorf, J Neurochem 46, 1412-1416 (1986)), so LOXCAT could reduce cerebral lactate/pyruvate ratio as well. Thus LOXACT can be used as a potential therapy for TBI related damages.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent (reduce risk of) onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Materials and Methods
The following materials and methods were used in the Examples below.
Chemical Reagents
Antimycin A, Oligomycin A, FMN, $NAD^+$, NADH, and ATP were purchased from sigma. DTT (Thermo R0862), protease inhibitor, EDTA-free (Roche 11873580001).
Preparation of DNA Constructs
Cloning of LOXCAT and $LOXCAT^{mut}$ into Vector pET30a
The plasmid containing LOXCAT and $LOXCAT^{mut}$ genes in vector pET30a were purchased from Genscript Corporation.

Cell Proliferation Assays
50,000 HeLa or K562 cells/well, or 25,000 C2C12 NDUFS4 KO cells/well were plated on a 6-well plate in pyruvate free media (5 mM glucose, no pyruvate, 200 μM uridine, penicillin/streptomycin, 10% dialyzed FBS). ETC inhibitor or pyruvate or the enzymes were added and cells were incubated for 72 h at 37° C. in 5% $CO_2$. At 72 h, cells were washed with 2 ml of PBS, trypsinized and counted using a Beckman Coulter Z2 coulter counter.
$NADH/NAD^+$ Measurement Assay
Total cellular $NADH/NAD^+$ were measured using NADH-glo assay (Promega, catalog number G9071). 200,000 cells/well were plated on a 6 well plate in pyruvate free media (5 mM glucose, no pyruvate, 200 μM uridine, penicillin/streptomycin, 10% dialyzed FBS). Next day, ETC inhibitor or pyruvate or the enzymes were added to the media and cells were incubated for 24 h at 37° C. in 5% $CO_2$. At 24 h cells were quickly washed with 1 ml of ice cold PBS and 500 μl of 1% DTAB solution was added to lyse cells. Manufacturer's instructions were followed hereafter. Briefly, 50 μl of this was then transferred to a PCR tube containing 25 μl 0.4M HCl (for $NAD^+$ measurement) or to an empty PCR tube (for NADH measurement). Both these samples were heated at 60° C. for 15 min to deplete $NAD^+$ or NADH. Samples were then left on bench for 10 min to cool down to room temperature before adding neutralizing solutions (25 μl of 0.5 M Tris base to the $NAD^+$ sample and 50 μl of 1:1=0.4M HCl: 0.5 M Tris base to the NADH sample). Samples were then vortexed and 30 μl of it was added to 30 μl of luciferase-reconstituted solution and incubated for 30 min at room temperature. Luminescence of samples were then measures on a Perkin Elmer Envision 2140 multiplate reader. Absolute concentrations of NADH and $NAD^+$ were determined against standard curves.
Media [Lactate]/[pyruvate] Measurements Using LCMS
500 μl media from the $NADH/NAD^+$ measurement experiment was drawn just before lysing cells. Media was then immediately filtered through a 10 kDa cutoff filter 500 μl centrifuge tubes (Amicon, Catalog number UFC501096) to get rid of any active enzyme. To 50 μl of this media 450 μl of 70% acetonitrile/water was added and incubated on ice for 30 min. Samples were then centrifuged at 14800 rpm for 20 min and 150 μl of centrifuged sample was transferred to LCMS vials. LCMS analysis was performed on an Agilent 1260 HPLC system coupled to Q Exactive Mass Spectrometer (ThermoFisher). Absolute concentrations of lactate and pyruvate were determined against standard curves.
Purification of LOXCAT and $LOXCAT^{mut}$ in *E. coli*
1 L culture of *E. Coli* BL21 (DE3) cells (Life Technologies, Catalog number C6010-03) transformed with pET30a vector containing LOXCAT (LOX from *Aerococcus viridans* and Catalase from *E. coli*) or $LOXCAT^{mut}$ genes were grown in 2.5 L flasks (IBI Scientific, Catalog number SS-8003) at 37° C. until O. D. (600 nm) of 0.4-0.6. The culture was then placed at 4° C. for at least an hour before moving it back to an 18° C. incubator for overnight induction with 250 μM 1-thio-β-d-galactoside (IPTG) (Sigma 15502). Along with IPTG, cells were supplemented with 1 mM 5-aminoluvilinic acid (Sigma 08339) and 300 μM Ferrous Ammonium Sulfate (Sigma 09719-250G) to assist heme biosynthesis. Next morning cells were harvested and frozen away until purified. For purification, cells were resuspended in 40 ml lysis buffer (50 mM sodium phosphate (pH 7.0), 150 mM NaCl, 0.1% Tween-20, 30 mM Imidazole, 2 mM DTT, 200 μM FMN, one Protease inhibitor complete EDTA-free (Roche 11873580001), 2.5 μl benzonase and 1 mg/ml lysozyme) per liter of culture and lysed by ultrasonication. After clarification of the lysate at 20,000 rpm for 30 min at 4° C., the lysate was bound to 5 ml Ni-sepharose beads/L of culture, washed with 10 column volume with washing buffer (50 mM sodium phosphate (pH 7.0), 100 mM NaCl, 0.1% Tween-20, 30 mM Imidazole, 10 mM $MgCl_2$, and 10 mM ATP) and eluted with elution buffer (50 mM sodium phosphate (pH 7.0), 150 mM NaCl, 300 mM Imidazole). Eluted fractions were then concentrated and ran through a HiTrapQFF ion exchange column (GE Healthcare, Catalog number GE17-5156-01) with a NaCl gradient of 100 mM to 1M. Pooled fractions from ion exchange was then passed thought a Superdex 200 increase column (GE Healthcare) in buffer containing 50 mM sodium phosphate (pH 7.0) and 150 mM NaCl. Pure fractions from gel filtration were concentrated using 15 ml 100 kDa MWCO filter centrifuge tubes (Millipore, Catalog number UFC910024) flash frozen in liquid nitrogen and frozen away at −80° C. Ion-exchange and gel filtration were performed on an AKTA pure FPLC system (GE Healthcare).

Measurement of LOXCAT's Ability to Quench 11202

Production of $H_2O_2$ was monitored using the Amplex red assay. $H_2O_2$ reacts with amplex red dye in presence of HPR to produce resorufin, a colored compound whose formation could be monitored by measuring absorbance at 570 mM. To measure Catalase's ability to quench $H_2O_2$ produced by LOX in LOXCAT using lactate as a substrate, increasing concentrations of lactate was incubated with LOXCAT in buffer (10 mM potassium phosphate, pH 7.0) for 20 min at 37° C. and measured the production of $H_2O_2$ using the amplex assay. As a control, 1 mM sodium azide was added to the reaction mixture, as azide inactivates catalase. In another experiment, to assess catalases capacity to break down $H_2O_2$, 50 µM of $H_2O_2$ was incubated with LOXCAT and measured $H_2O_2$ concentrations after 20 min of incubation.

Measurement of LOXCAT's Ability to Convert Lactate to Pyruvate

Ability of lactate oxidase in LOXCAT to convert lactate into pyruvate was assessed by incubating increasing concentrations of lactate with LOXCAT in buffer (10 mM potassium phosphate, pH 7.0) for 20 min at 37° C., followed by measuring pyruvate concentrations using LCMS at the end of the reaction.

Ex Vivo Activity Measurement of LOXCAT in Mouse Blood

250 µl of EDTA-treated mouse blood was plated in each well of a 24 well plate. buffer, LOXCAT or LOXCAT$^{mut}$ (40 µg each) were added then added to the wells. At different time points 25 µl of this blood sample was drawn and 450 µl of 70% acetonitrile/water was added and incubated on ice for 30 min. Samples were then centrifuged at 13000 rpm for 20 min and 150 µl was transferred to LCMS vials. LCMS analysis was performed on an Agilent 1260 HPLC system coupled to Q Exactive Mass Spectrometer (ThermoFisher). Absolute concentrations of lactate and pyruvate were determined against standard curves.

Ex Vivo Stability of LOXCAT in Mouse Blood

250 µl of EDTA-treated mouse blood was plated in each well of a 24 well plate. To this samples buffer, LOXCAT or LOXCAT$^{mut}$ (40 µg each) were added. At different time points 5 µl of this blood sample was drawn and the integrity of LOXCAT was tested by western blot against anti-his6 antibody, as LOXCAT and LOXCAT$^{mut}$ contain an N-terminal $His_6$-tag.

In Vivo Activity of LOXCAT in Mouse Blood

Animal studies followed protocols approved by the MGH Institutional Animal Care and Use Committee. Wild type mice of various background were obtained from Jackson Laboratory. Anesthetized (Sevoflurane) animals were injected with either 250 µl of buffer (50 mM sodium phosphate (pH 7.4), and 150 mM NaCl) that LOXCAT is dissolved in as a control, or 250 µl (41 mg/kg) of LOXCAT or 250 µl (41 mg/kg) of LOXCAT$^{mut}$ into the tail vein. Animals were then kept under anesthesia for another 15 min to let enzyme react. At 15 min blood was collected by tail snipping, immediately added to 70% ice-cold acetonitrile to quench any enzyme reaction. This sample was then incubated on ice for another 30 min to precipitate out proteins. Samples were then centrifuged at 14000 rpm for 20 min and supernatant was withdrawn for mass spectrometric analysis of blood lactate and pyruvate. Absolute concentrations of lactate and pyruvate were obtained by comparing them against a standard curve.

The Cardiac Arrest (CA)/Cardiopulmonary Resuscitation (CPR) Model

Animal studies followed protocols approved by the MGH Institutional Animal Care and Use Committee. Cardiac arrest (CA) and cardiopulmonary resuscitation (CPR) was performed as previously described with minor modification (Ikeda et al). Beriefly, Black 6/j mice were anesthetized with 5% isoflurane in 100% oxygen and intubated. Mice were ventilated (MiniVent ventilator, Harvard Apparatus, Holliston, Mass.) and maintained with 1.5% isoflurane. Catheters (PE-10, Becton Dickinson, Franklin Lakes, N.J.) were inserted into the left femoral artery and vein via a midline thigh incision. Arterial blood pressure was measured via the left femoral arterial line. Blood pressure, body temperature, and needle-probe ECG monitoring data were recorded.

CA was induced by injection of potassium chloride (0.08 mg/g body weight) via the left femoral vein and ventilation was stopped. Mice were subjected to CA and received either 150 µg/g body weight of LOXCAT, LOXCAT$^{mut}$, or vehicle 2 min before CPR in a randomized and blinded manner via the left femoral vein. After 8 min of CA, chest compression was delivered with a finger at the rate of 300-350 bpm. Ventilation with 100% oxygen and infusion of epinephrine (0.6 µg/min) was initiated 30 s before CPR, and the infusion was continued until the heart rate became >300 bpm. Return of spontaneous circulation (ROSC) was defined as the return of sinus rhythm with mean arterial pressure >40 mmHg lasting at least 10 s. Core body temperature was maintained at 37.0±0.2° C. by a lamp throughout the surgical procedure until 1 h after ROSC. Mice were extubated, and catheters were removed 1 h after ROSC. Then, mice were transferred to the cage which was maintained at 30° C. by a lamp for 2 h. Mice were then monitored for next 10 days for survival.

Example 1

Figure 2A:
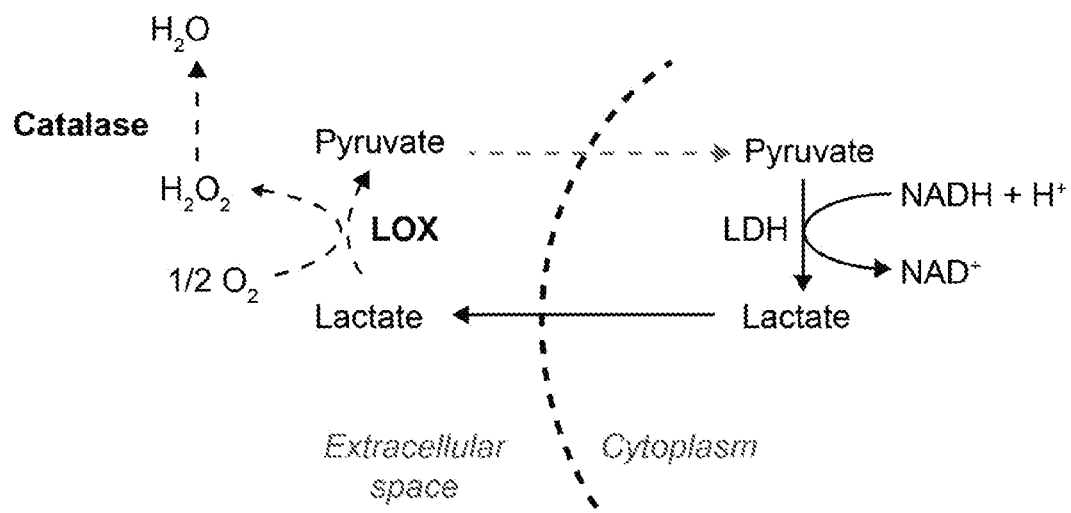
FIGS. 2A-C. Combined action of extracellular of lactate oxidase (LOX) and catalase (CAT) modulates the intracellular NADH/NAD⁺ ratio. (A) A schematic showing the relationship between the extracellular [lactate/[pyruvate] ratio and the cytoplasmic [NADH]/[NAD+] ratio. Decrease in extracellular [lactate/[pyruvate] ratio will result in a decrease in cytoplasmic [NADH]/[NAD+]. The combination of extracellular LOX and Catalase reduces (B) the media [lactate/[pyruvate] ratio and (C) cytoplasmic [NADH]/[NAD+] by 1.7-fold from antimycin-treated cells. This changes in [NADH]/[NAD+] ratio is comparable to addition of 1 mM sodium pyruvate in the media. Data are mean±S.D., n=3. Student's t-test P<0.01 and *P<0.001.
Figure 2B:
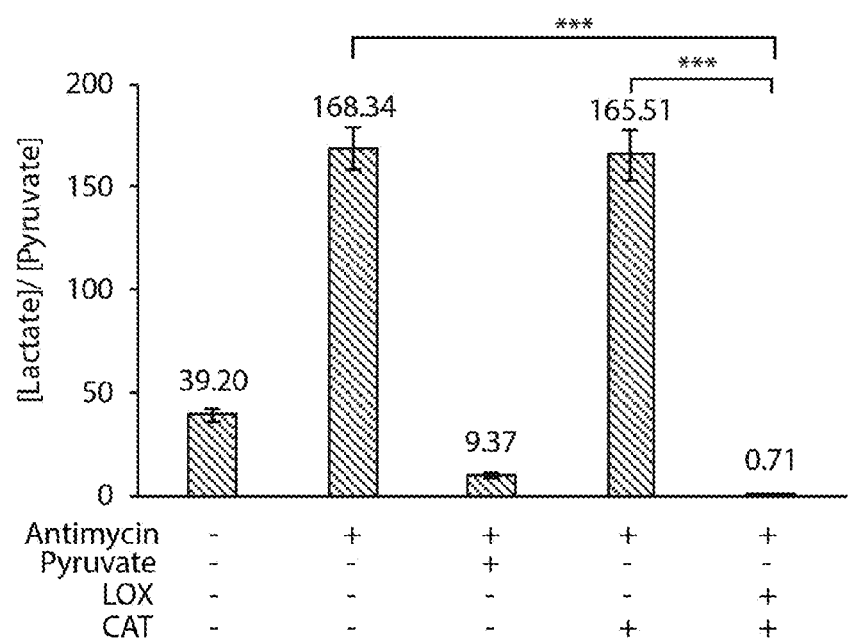
Figure 2C:
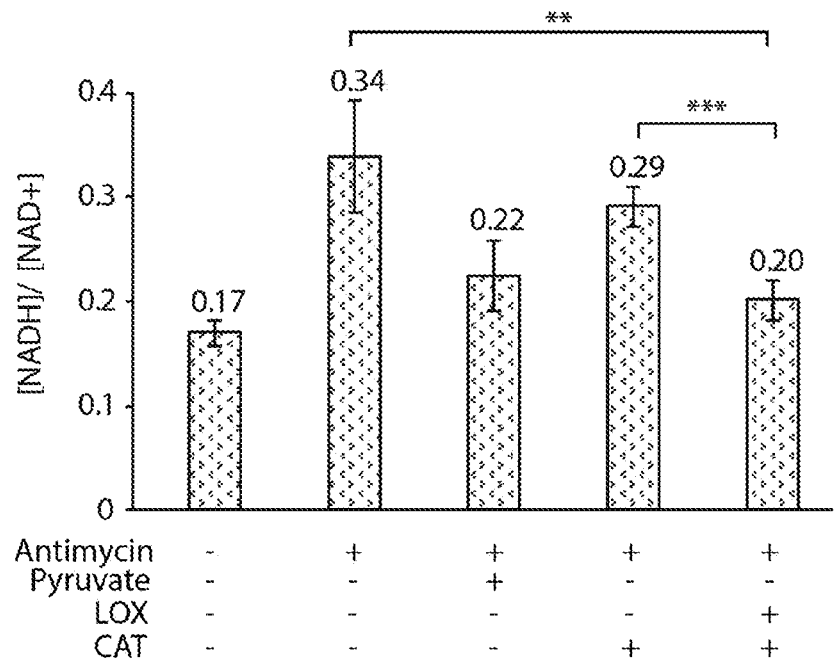

A Combination of Extracellular Lactate Oxidase (LOX) and Catalase (CAT) Reduce Media Lactate/Pyruvate and Total Cellular NADH/NAD$^+$ We first tested if a combination of extracellular lactate oxidase (LOX) and catalase (CAT) could modulate the total cellular [NADH]/[NAD$^+$] by affecting the extracellular [lactate]/[pyruvate] ratio. As seen in FIG. 2(B) antimycin, an inhibitor of mitochondrial electron transport chain complex III, increases the extracellular [lactate]/[pyruvate] ratio by 1.5-fold in 24 h because the cells under these conditions rely on glycolysis for ATP generation, which results in excessive lactate production by the LDH reaction to keep a healthy NAD$^+$ concentration for running glycolysis (FIG. 1(A)). Addition of pyruvate could reduce this ratio by 18-folds in antimycin-treated cells. In comparison, extracellularly added LOX or LOX and CAT could reduce this ratio by almost 230-folds, meaning that LOX is effectively converting a large fraction of the extracellular lactate into pyruvate. Catalase alone has no effect on the lactate/pyruvate ratio, as we anticipated. These changes in the [lactate]/[pyruvate] ratio correlates well with the changes in the total cellular [NADH]/[NAD$^+$] in cells from the above experiment. FIG. 2(C) shows that antimycin treatment increases total the cellular [NADH]/[NAD$^+$] ratio by 2-fold in 24 h. This ratio is reduced by pyruvate by approximately 1.5-fold and a similar fold reduction in the [NADH]/[NAD$^+$] ratio was observed in the LOX and CAT treated cells. The [NADH]/[NAD$^+$] ratio could not be calculated in LOX only-treated cells as most cells died, presumably because of the toxic $H_2O_2$ produced in the LOX reaction, making the concentrations of NADH and NAD$^+$ too low to accurately detect. Catalase alone has no effect on the [NADH]/[NAD$^+$] ratio. These data suggest that extracellular LOX and CAT could modulate the total cellular [NADH]/[NAD$^+$] ratio by manipulating the extracellular [lactate]/[pyruvate] ratio likely by shifting the equilibrium of the LDH reaction towards lactate production, as we hypothesized.

Example 2

A Combination of Extracellular Lactate Oxidase (LOX) and Catalase (CAT) Restores Proliferative Defects in Mitochondrial Dysfunction We next sought to determine if the reduction of the [NADH]/[NAD$^+$] ratio by extracellular LOX and CAT could rescue cell proliferation in the settings of mitochondrial dysfunction. For this purpose, we tested if we could rescue proliferative defects in HeLa cells with chemically-induced RCD. Cells with RCD proliferate poorly unless they are supplemented with pyruvate (King and Attardi, 1989). This pyruvate auxotrophy in cells without RC function is thought to be due to the role of pyruvate in re-oxidizing cytoplasmic NADH in the LDH reaction (Titov et al., 2016). We grew wild type HeLa cells in pyruvate-free media containing antimycin, an inhibitor of the mitochondrial respiratory chain complex III (FIG. 3(A), at a dose that maximally inhibits the respiratory chain. As can be seen in FIG. 3(B), cells cannot grow unless pyruvate is supplemented in the media. LOX (from *Aerococcus viridans*) alone added to the media exacerbates antimycin toxicity, presumably due to $H_2O_2$ generation, and catalase (from bovine liver) alone has no effect. However, the combination of LOX and CAT in the media significantly rescues cell growth for up to 4 days (FIG. 3(B)). This proves that the combination of lactate oxidase and catalase could substitute for the need for supplemented pyruvate in RCD models for cell proliferation.

Figure 3A:
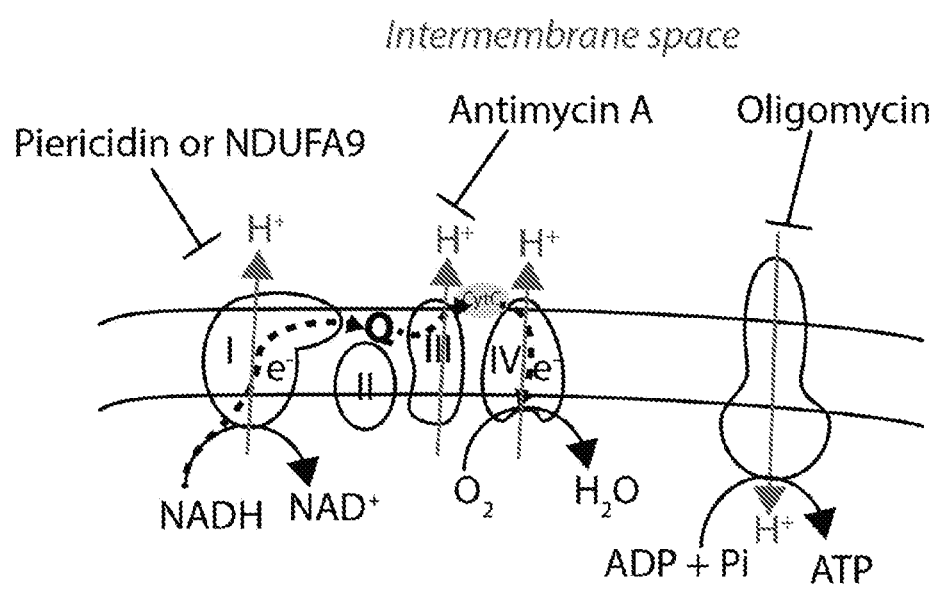
FIGS. 3A-E. Combined action of extracellular lactate oxidase (LOX) and catalase (CAT) restores proliferative defects in in chemical and genetic models of mitochodrial dysfunction. Cells with mitochondrial respiratory chain dysfunction (RCD) need pyruvate in their media for proliferation. In this assay cells with RCD were grown in the presence of the LOX or/and CAT in pyruvate free media for 72 h and counted cell numbers. (A) Depicts different mitochondrial electron transport chain inhibitors that are used in this assay. (B) A combination of extracellular LOX and CAT rescues growth rates in antimycin (Complex III inhibitor)-treated cells. Media supplemented with LOX and CAT restore proliferative defects (C) induced by different mitochondrial electron transport chain inhibitors, (D) in a different cell line, and (E) in genetic model of mitochondrial RCD. Data are mean±S.D., n=3. Student's t-test P<0.01 and *P<0.001.
Figure 3B:
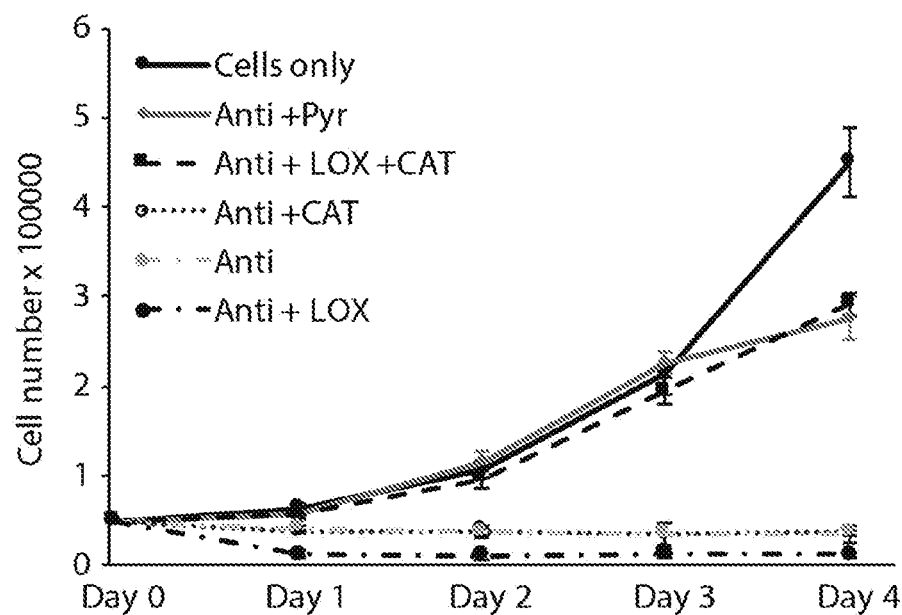
Figure 3C:
Figure 3D:
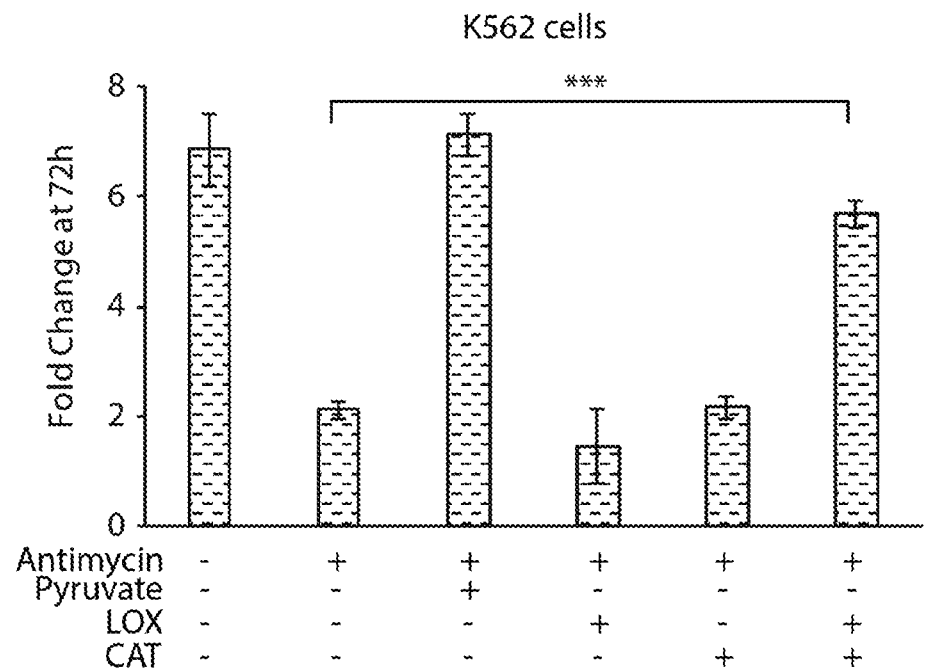
Figure 3E:
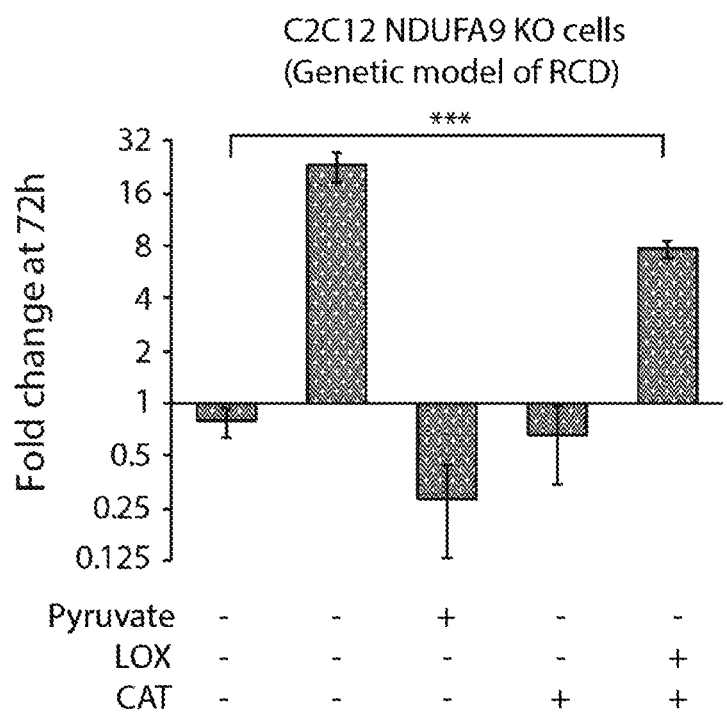

HeLa cells treated with complex I inhibitor piericidin and complex IV inhibitor oligomycin (FIG. 3(A)) exhibited significant cell growth rescue when LOX and CAT were added to their media (FIG. 3(C)), suggesting that LOX and CAT mediated cell rescue is not only complex I specific. We also observed comparable rescue effects in antimycin-treated myelogenous leukemia cell line K562 (FIG. 3(D)). Similarly, LOX and CAT in the media also corrected growth defects in a genetic model of mitochondrial dysfunction (FIG. 3(E)). These data suggest that our approach is not limited to only one cell type or only a particular type of mitochondrial dysfunction.

Example 3

Figure 4A:
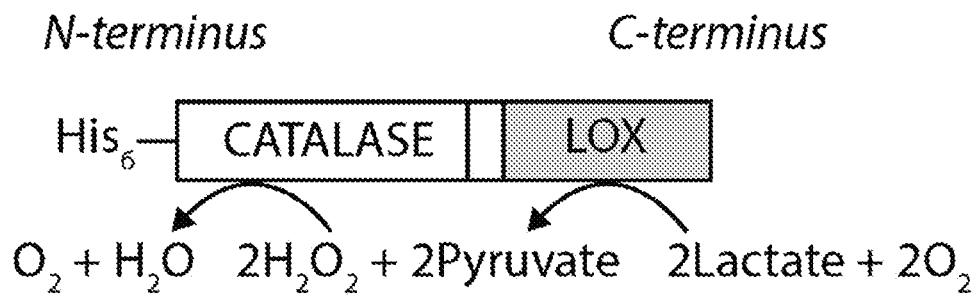
FIGS. 4A-F. LOXCAT: an exemplary engineered fusion of lactate oxidase and catalase. (A) Design of the $His_6$-tagged fused LOXCAT and LOXCAT$^{mut}$ constructs (B) Recombinant wild type LOXCAT and catalytically dead LOXCAT$^{mut}$ could be purified after overexpression in *E. coli*. (C) Purified LOXCAT, but not the LOXCAT$^{mut}$, converts lactate into pyruvate. (D) LOXCAT does not produce significant $H_2O_2$ with up to 10 mM lactate, a concentration that is higher than what is detected in RCD patient blood, measured in an amplex red fluorescence assay. However, a substantial increase in amplex red fluorescence was observed when sodium azide, an inhibitor of catalase, was incubated in the reaction of LOXCAT and lactate. (E) Recombinant LOXCAT could quench 100 μM of $H_2O_2$ in a sodium azide-sensitive manner. (F) Only wild type LOXCAT but not the catalytically dead variant LOXCAT$^{mut}$ could consume oxygen in presence of lactate. This oxygen consumption is Catalase sensitive.
Figure 4A:
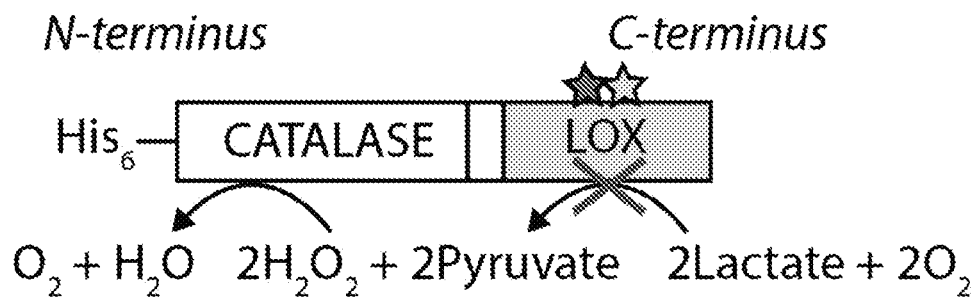
Figure 4B:
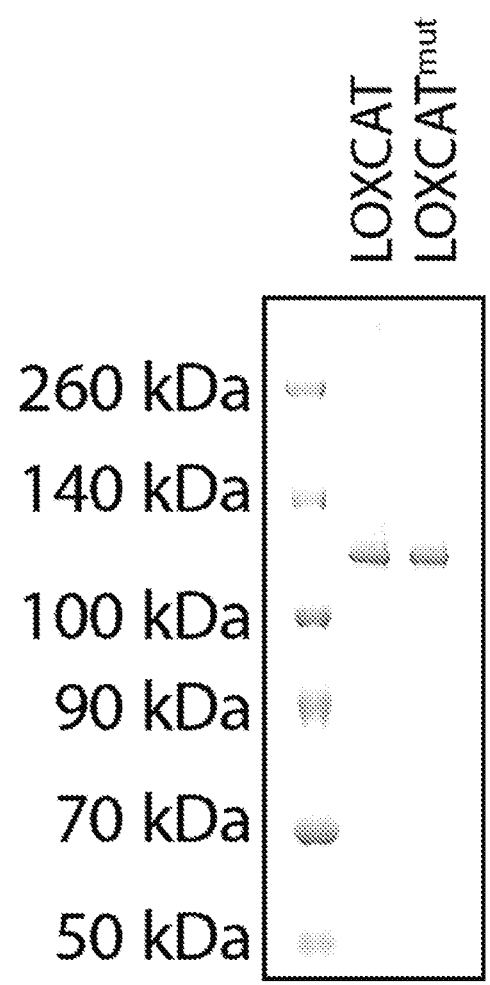

Design of a Single Polypeptide Containing Lactate Oxidase (LOX) and Catalase (CAT) for In Vivo Applications To facilitate future in vivo applications, we engineered a fusion of lactate oxidase and catalase into a single polypeptide that we call LOXCAT (FIG. 4(A)), (Andre et al., 2013; Li et al., 2007; Melik-Adamyan et al., 2001; Taurino, 2013). We hypothesized that an engineered fusion of the two enzymes would be more effective in quenching potential $H_2O_2$ leakage from the lactate oxidase reaction, as—(1) LOX and CAT could have different diffusion rates, and (2) catalase could get cleared faster from the bloodstream than LOX. This LOXCAT construct contains a His$_6$-tag at the N-terminus of catalase from *E. coli* (molecular weight 84 kDa) which is then connected to the N-terminus of lactate oxidase from *Aerococcus viridans* (molecular weight 40 kDa) using an L20 linker (Andre et al., 2013; Martin et al., 2005) (FIG. 4(A)). The sequence of the amino acid residues of this fusion protein is shown above. We observed overexpression of this recombinant protein in bacteria upon IPTG induction (FIG. 4(B)) and could measure its activity in converting lactate into pyruvate in buffer (FIG. 4(C)). This purified construct does not produce any $H_2O_2$ at up to 10 mM of lactate, a concentration which is higher than usual blood lactate concentrations even in mitochondrial dysfunction (FIG. 4(D)). To test if catalase in the fusion protein is responsible for detoxifying $H_2O_2$ when lactate is incubated, we repeated the reaction in presence of sodium azide, an inhibitor of catalase, and see significant increase in $H_2O_2$ leakage from the reaction (FIG. 4(D)). Also, this construct could quench 50 µM of $H_2O_2$ in 10 min as much as catalase in the tested conditions (FIG. 4(E)). These data suggest that the designed LOXCAT could effectively convert lactate into pyruvate and does not produce any detectable $H_2O_2$ under these experimental conditions and also this protein construct could quench externally added hydrogen peroxide meaning both LOX and CAT in the fusion protein are active.

Figure 4C:
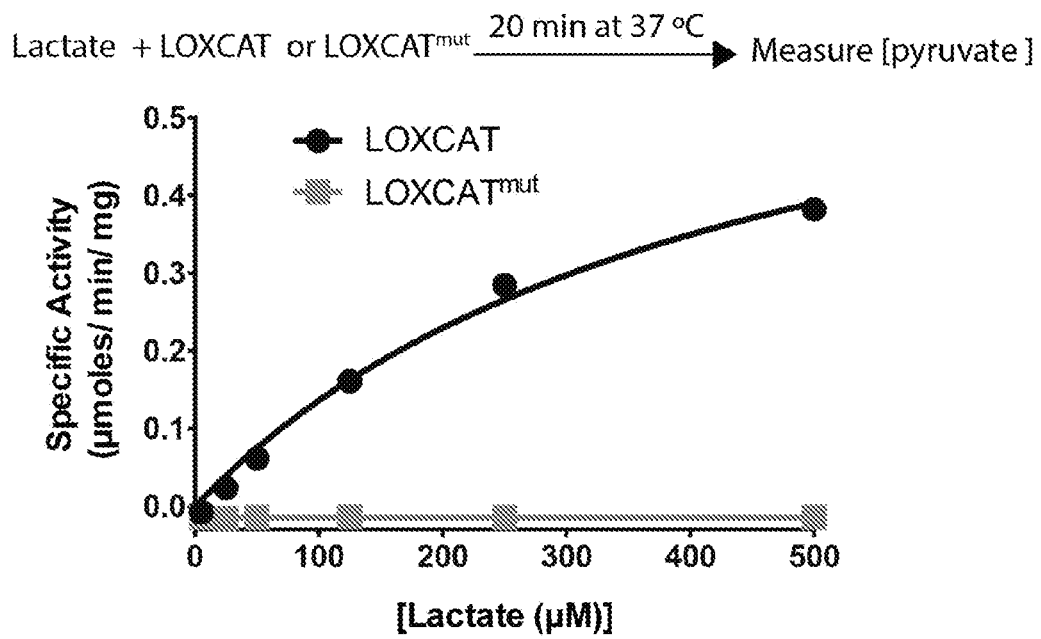
Figure 4D:
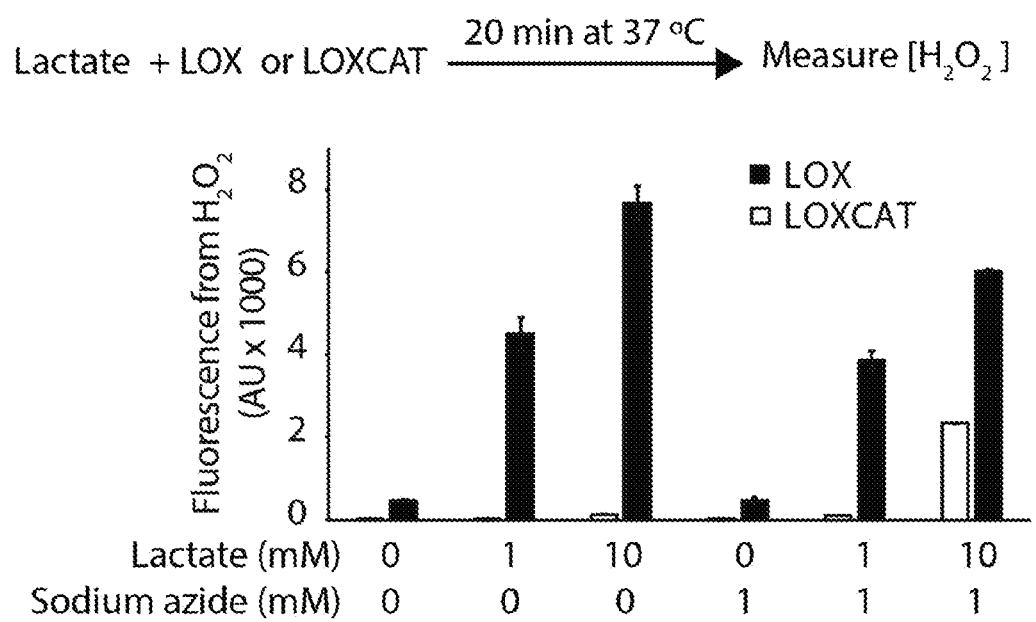
Figure 4E:
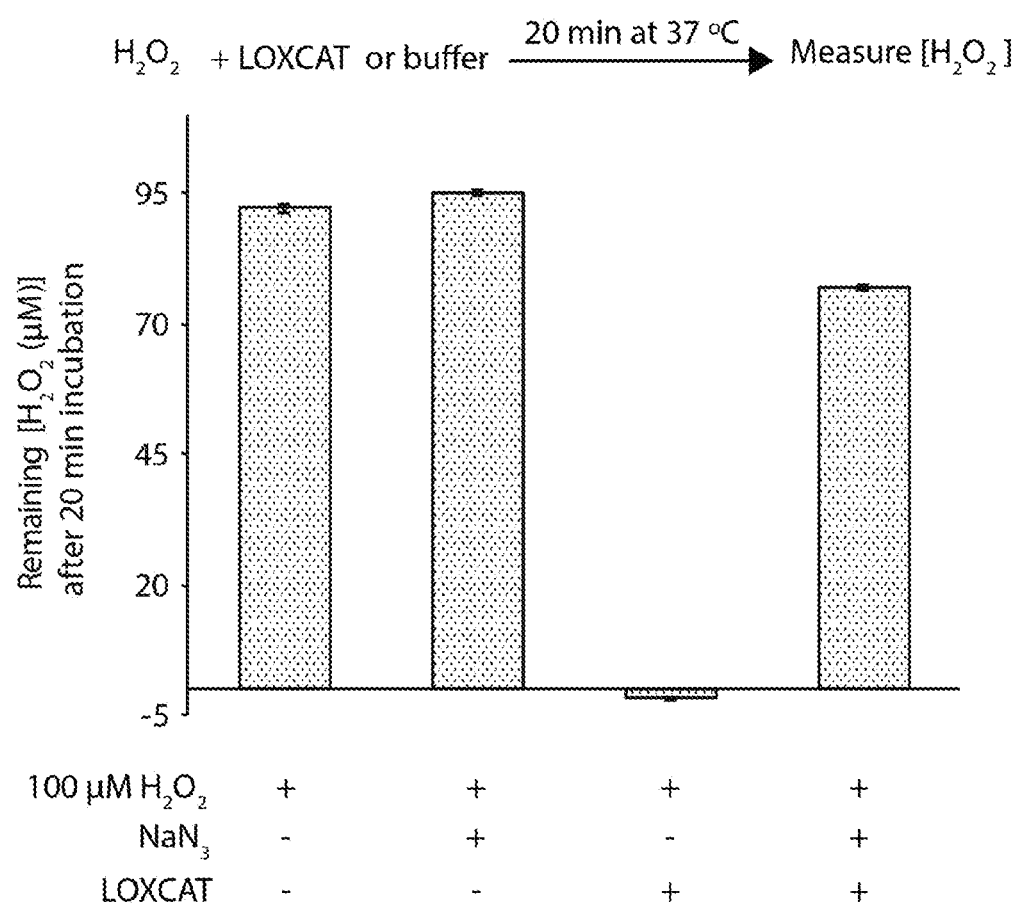
Figure 4F:
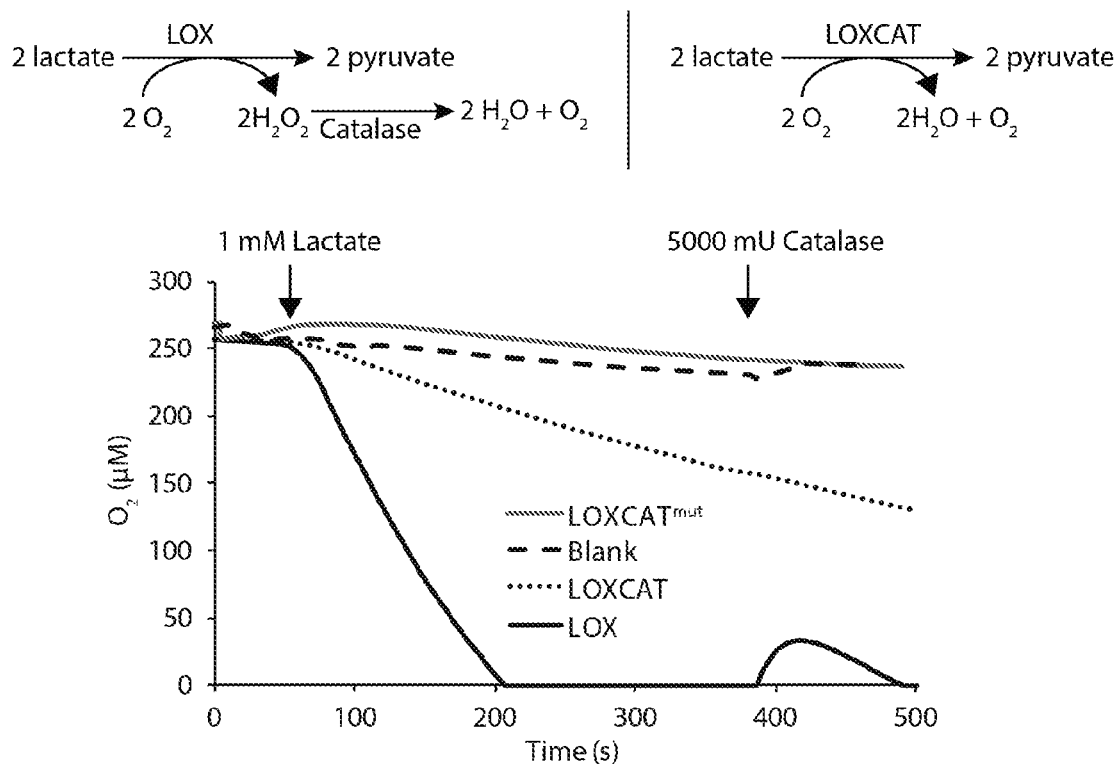

We next designed an enzymatically dead version of LOXCAT where LOX is inactivated by mutating catalytically important residues histidine 265 and arginine 268 to alanine residues (H265A and R268A) (FIG. 4(A)). This mutant LOXCAT could serve as a negative control for our cell assays. As seen in FIGS. 4(C) and 4(F), only the wild type LOXCAT, but not the mutant version is capable of converting lactate into pyruvate.

Example 4

Figure 5A:
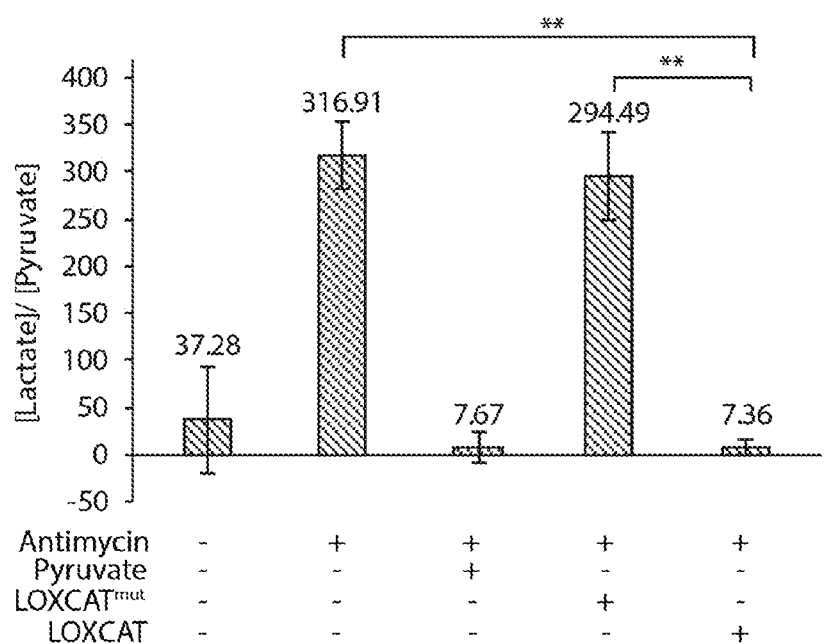
FIGS. 5A-F. Overcoming reductive stress with a single engineered polypeptide LOXCAT. Purified LOXCAT added to the media reduce (A) the extracellular [lactate]/[pyruvate] and (B) the total cellular [NADH]/[NAD⁺] ratio in antimycin-treated HeLa cells. (C) Proliferative defects induced by antimycin in HeLa cells are rescued when cells are incubated with the LOXCAT but not with LOXCAT$^{mut}$. LOXCAT in media also rescues cell proliferation in (D) K562 cells treated with antimycin, (E) a genetic model of RCD and (F) HeLa cells treated with piericidin and oligomycin. These rescues are comparable to 1 mM pyruvate-mediated cell growth rescue. Data are mean±S.D., n=3. Student's t-test P<0.01 and *P<0.001.
Figure 5B:
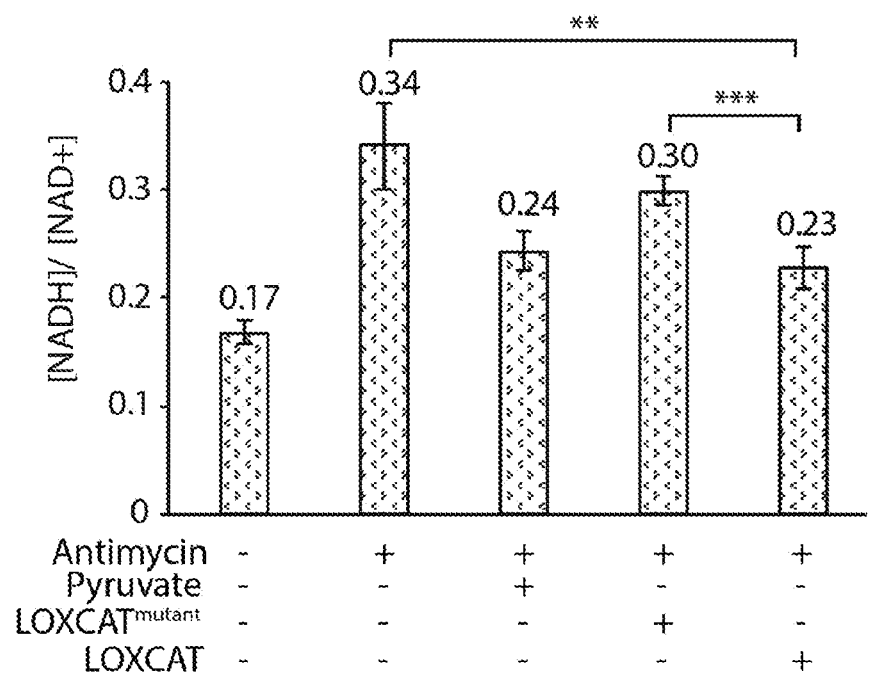
Figure 5C:
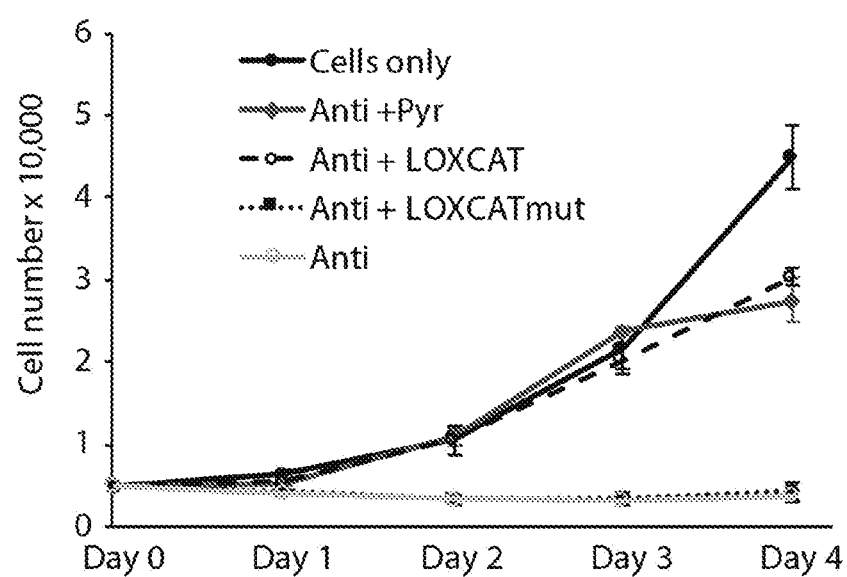
Figure 5D:
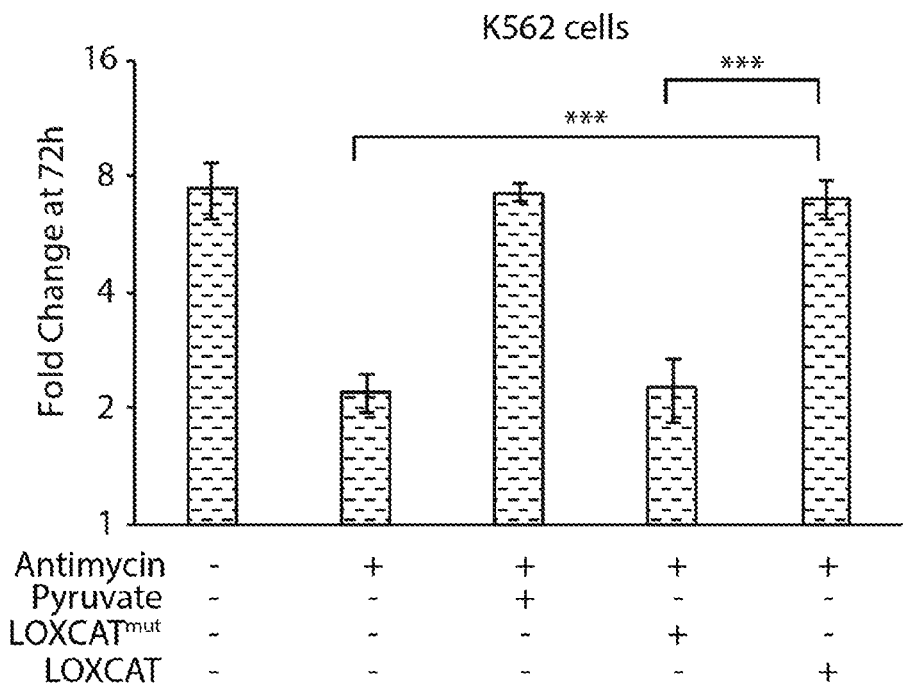
Figure 5E:
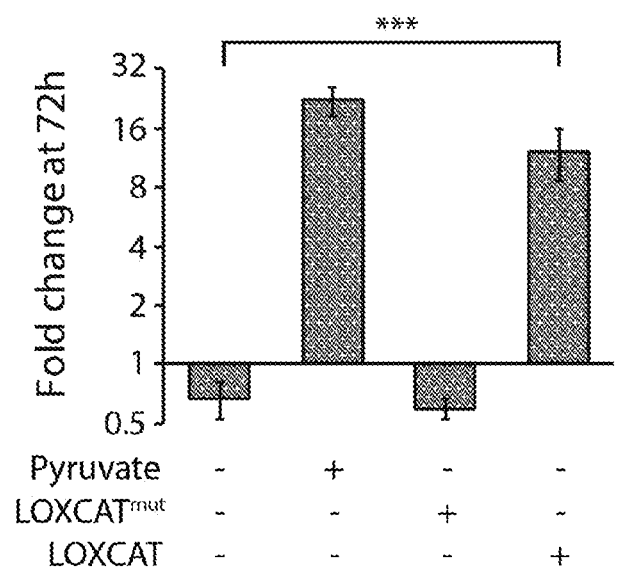
Figure 5F:
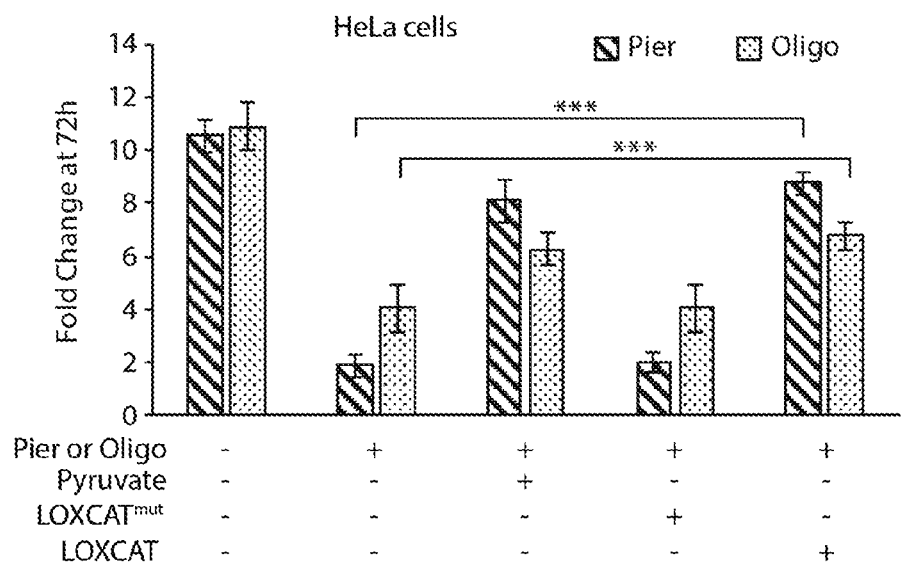

Engineered Single Polypeptide LOXCAT Reduces [lactate]/[pyruvate], [NADH]/[NAD$^+$] and Restores Proliferative Defects in Mitochondrial Dysfunction To examine if this protein construct is active in cell culture, we tested if LOXCAT could reduce the [NADH]/[NAD$^+$] ratio in cells by converting extracellular lactate into pyruvate. We observed that the fusion LOXCAT could recapitulate the effects of separately added LOX and CAT in affecting the extracellular [lactate]/[pyruvate] (FIG. 5(A)) and thereby reducing [NADH]/[NAD$^+$] ratio by 1.3-fold from antimycin-treated HeLa cells (FIG. 5(B)). Notably, the mutant LOXCAT (LOXCAT$^{mut}$) does not change the [lactate]/[pyruvate] and [NADH]/[NAD$^+$] ratio from antimycin-treated control cells (FIGS. 5(A) and (B)). Next, we incubated the purified wild type and the mutant LOXCAT with HeLa cells in pyruvate free media containing antimycin. As shown in FIG. 5(C) antimycin-treated cells have significantly reduced growth rate and pyruvate could rescue this growth phenotype. Our fused wild type LOXCAT could rescue growth rates as much as pyruvate, whereas the mutant version is ineffective in doing so (FIG. 5(C)). Moreover, LOXCAT could rescue cell proliferation in a different cell line (FIG. 5(D)), in a generic model of mitochondrial dysfunction (FIG. 5(E), and in HeLa cells treated with piericidin and oligomycin (FIG. 5(F)) indicating that LOXCAT is capable of rescuing proliferative defects in different mitochondrial dysfunctions and across different cell lines. It is noteworthy that LOXCAT$^{mut}$ did not rescue cell proliferation in any of the above experiments. These results suggest that the designed fusion protein is capable of ameliorating reductive stress in mitochondrial dysfunction. This construct could be used for further in vivo testing of our approach.

Example 5

Ex Vivo Efficacy of the Fusion Enzyme

Figure 6A:
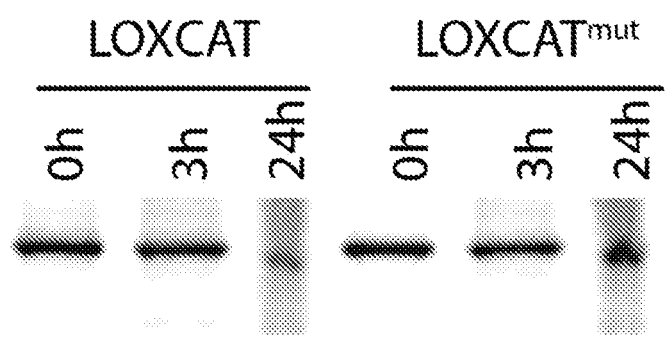
FIGS. 6A-B. Ex vivo efficacy of LOXCAT. (A) An anti-$His_6$ western blot shows that the integrity of both wild type $His_6$-LOXCAT and mutant $His_6$-LOXCAT$^{mut}$ remain intact in blood in a dish up for to 24 h. (B) Purified LOXCAT, but not LOXCAT$^{mut}$, reduces the [lactate]/[pyruvate] ratio in whole blood over time.
Figure 6B:
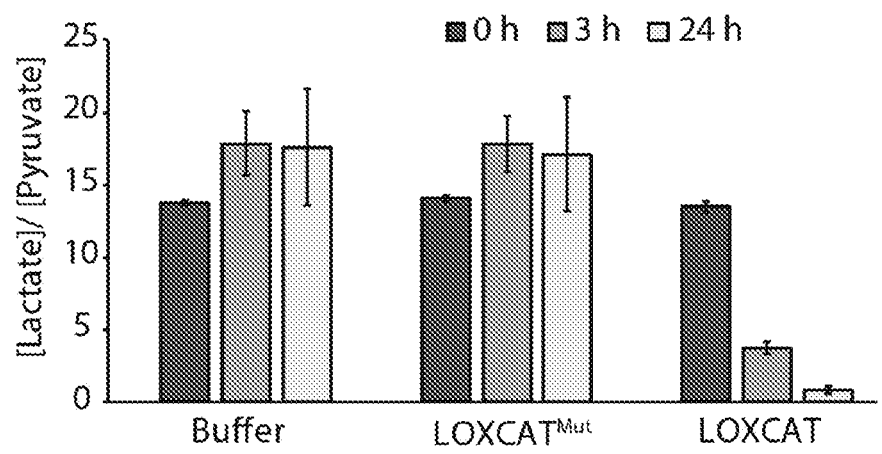

The ultimate goal of this project is to intravenously administer LOXCAT into patient blood to reduce lactic acid burden and reductive stress in certain diseases, including mitochondrial dysfunction. Before testing in vivo we wanted to examine if the enzyme is active and stable in fresh mouse blood ex vivo. We incubated 40 μg of LOXCAT or LOXCAT$^{mut}$ in 250 μl of blood drawn from a wild type mouse and monitored the [lactate]/[pyruvate] ratio and tested protein degradation using western blot over time. We used LCMS to measure absolute concentrations of lactate and pyruvate at different time points and an anti-His$_6$ antibody for western blots as LOXCAT contains an N-terminal His$_6$-tag. As seen in FIG. 6(A) we could detect significant amount of the both LOXCAT and LOXCAT$^{mut}$ even at 24 h. This demonstrates robust stability of fused LOXCAT against endogenous blood proteases, as the blood proteases should still be active in whole blood used in this experiment. We also saw a drastic decrease in the [lactate]/[pyruvate] over time (FIG. 6(B)). The mutant control failed to change the [lactate]/[pyruvate] ratio from the no enzyme treated blood sample. This preliminary data suggests that LOXCAT is stable in whole mouse blood at least for up to 24 h and could reduce the [lactate]/[pyruvate] ratio by at least 10-fold at 24 h.

Example 6

In Vivo Efficacy of the Fusion Enzyme

Figure 7A:
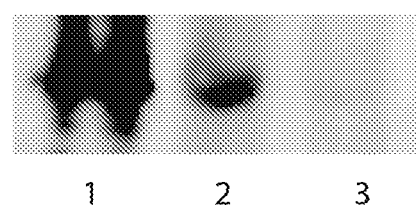
FIGS. 7A-B. In vivo efficacy of LOXCAT. (A) LOXCAT is stable in the bloodstream for 30 min.
Figure 7B:
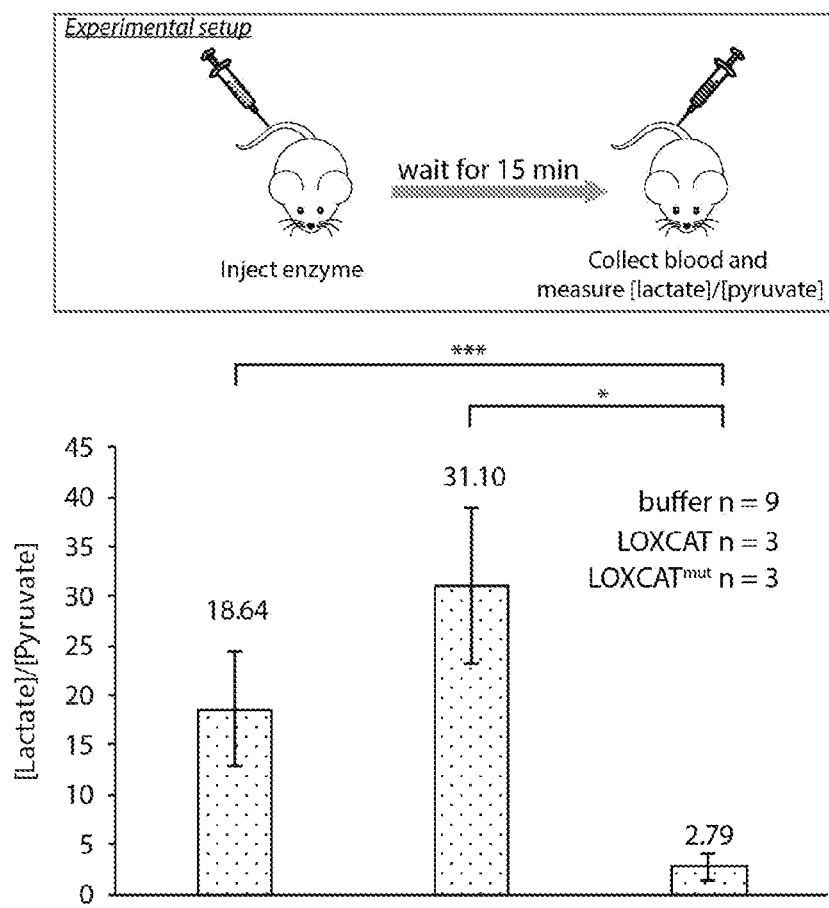

To test the efficacy of the LOXCAT enzyme in vivo, we first assessed how long the enzyme remains intact in the bloodstream post-injection. We observed that the enzyme remains in the circulation for at least 30 min (FIG. 7A). Next, we tested if an injection of LOXCAT could reduce the blood [lactate]/[pyruvate] ratio, as we hypothesized. We decided to examine the effect of LOXCAT at 15 min post-injection because we postulate to see highest impact of LOXCAT at this time point. We observe that LOXCAT reduces the blood [lactate]/[pyruvate] ratio by 6-fold from control (buffer injected) mice at 15 min post-injection (FIG. 7B). As shown in FIG. 7B, LOXCAT$^{mut}$ does not reduce the blood [lactate]/[pyruvate]. Mice injected with the enzymes maintained normal body temperature and heart rate.

LOXCAT almost disappears from the bloodstream at 3 h (FIG. 7A). We are currently trying to extend the half-life of the enzyme in the bloodstream. For this purpose, we are testing serum stability of LOXCAT tagged with albumin binding peptide.

After obtaining an optimal serum stability using one of the strategies described in the section "Methods of delivering LOX+CAT or LOXCAT to patients" the efficacy of LOXCAT is tested in various disease models such as models of acute lactic acidosis, sepsis, mitochondrial dysfunction. We will use NDUFS4 knock out mice as a model for mitochondrial dysfunction. These mice lack mitochondrial complex I function and recapitulate the phenotypes of Leigh's syndrome, the most common infantile mitochondrial dysfunction (Quintana et al., 2010). Recently, hypoxia has been evaluated as a treatment option for mitochondrial disease in these mice (Jain et al., 2016). NDUFS4 KO mice present the disease phenotype on about 40 days and usually die within 50-60 days. We will administer LOXCAT on day 40 using the dosage obtained from the initial studies with wild type mouse and monitor if the enzymes could prolong lifespan, help regain weigh and body temperature, prevent blindness and loss of neuronal activities in the NDUFS4 KO mice. For sepsis, we will use a lipopolysaccharide (LPS)-induced sepsis mouse model and monitor blood pH and [lactate]/[pyruvate] post LOXCAT injection.

Example 7

Cardiac Arrest

To test whether acute reduction of blood lactate/pyruvate ratio will benefit in a disease model, we performed experiments testing whether reduction in the circulating lactate/pyruvate ratio improved survival in a CA/CPR model. We induced cardiac arrest by injecting potassium chloride (0.08 mg/g body weight) into the femoral vein in black6/J mice and performed cardiopulmonary resuscitation (CPR) as previously described by Ikeda et al (Resuscitation 105, 138-144 (2017)). Only 30% of the mice post CPR survived at day 10 in this model. LOXCAT (150 μg/g) or vehicle was injected into the femoral vein 2 minutes before performing CPR. Blood was also collected at 60 min after ROSC from the left femoral artery to measure the circulating lactate/pyruvate ratio and to ensure LOXCAT activity.

Figure 9A:
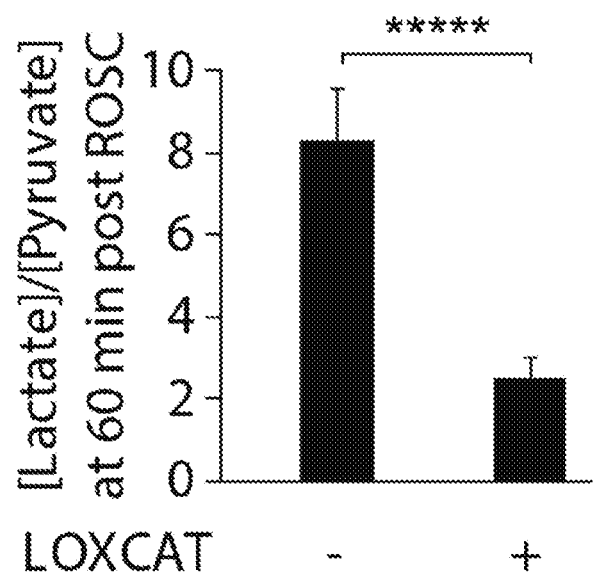
FIGS. 9A-D. Effect of LOXCAT on a cardiac arrest (CA)/Cardiopulmonary resuscitation (CPR) model: Effect of LOXCAT on the circulating (A) lactate/pyruvate ratio, (B) lactate, and (C) pyruvate at 60 min post return of spontaneous circulation (ROSC). (D) Effect of LOXCAT on survival post CA/CPR. Data are mean±S.D., n=10. Student's t-test *P<0.05 and *****P<0.00001.
Figure 9B:
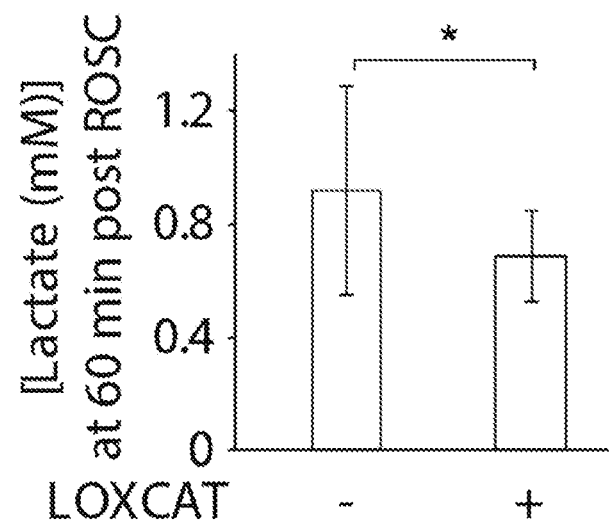
Figure 9C:
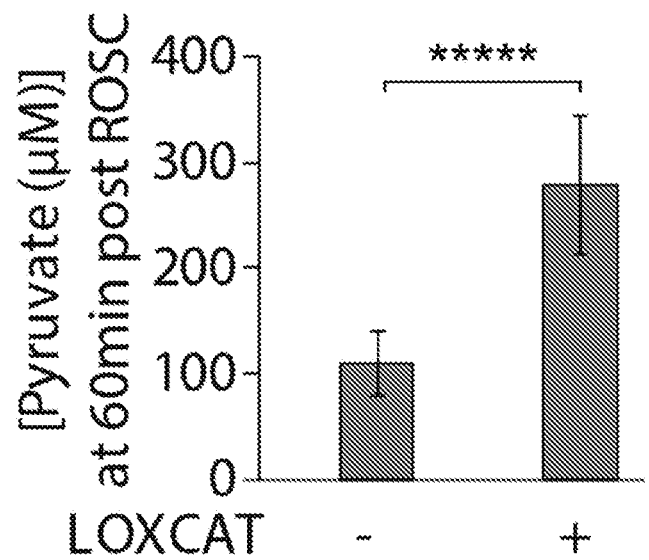
Figure 9D:
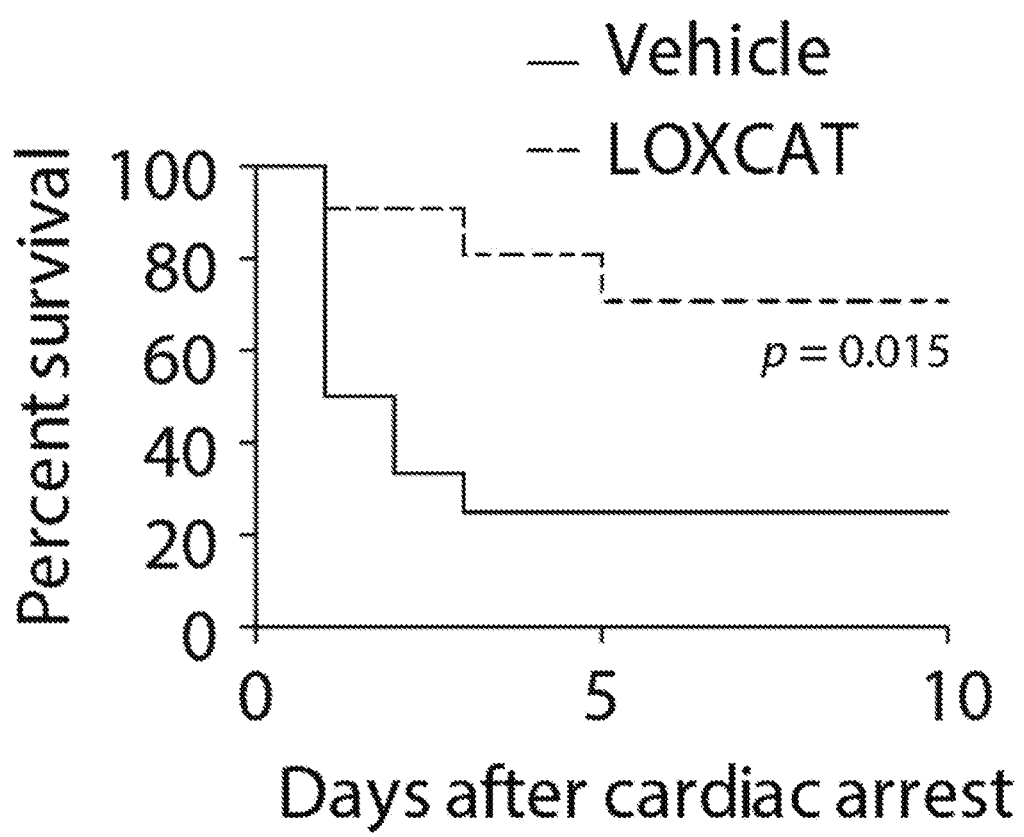

The results showed that LOXCAT reduced the circulating lactate/pyruvate ratio from 8.3 to 2.5 (FIG. 9A), both by reducing the lactate concentration by 1.3-fold and increasing the pyruvate concentration by 2.5-fold (FIGS. 9B and 9C). LOXCAT treated mice improved the survival rate from 25% in the vehicle to 70% at 10 days (FIG. 9D). This experiment showed the in vivo potential of LOXCAT for acute indications.

REFERENCES

Acharya, A. P., Rafi, M., Woods, E. C., Gardner, A. B., and Murthy, N. (2014). Metabolic engineering of lactate dehydrogenase rescues mice from acidosis. Sci Rep 4, 5189.

Alpar, H. O., and Lewis, D. A. (1985). Therapeutic efficacy of asparaginase encapsulated in intact erythrocytes. Biochem Pharmacol 34, 257-261.

Andre, C., Kim, S. W., Yu, X. H., and Shanklin, J. (2013). Fusing catalase to an alkane-producing enzyme maintains enzymatic activity by converting the inhibitory byproduct H2O2 to the cosubstrate O2. Proceedings of the National Academy of Sciences of the United States of America 110, 3191-3196.

Bakker, J., Coffernils, M., Leon, M., Gris, P., and Vincent, J. L. (1991). Blood lactate levels are superior to oxygen-derived variables in predicting outcome in human septic shock. Chest 99, 956-962.

Blanco, E., Bey, E. A., Khemtong, C., Yang, S. G., Setti-Guthi, J., Chen, H., Kessinger, C. W., Carnevale, K. A., Bornmann, W. G., Boothman, D. A., et al. (2010). Beta-lapachone micellar nanotherapeutics for non-small cell lung cancer therapy. Cancer Res 70, 3896-3904.

Boumezbeur, F., Petersen, K. F., Cline, G. W., Mason, G. F., Behar, K. L., Shulman, G. I., and Rothman, D. L. (2010). The contribution of blood lactate to brain energy metabolism in humans measured by dynamic 13C nuclear magnetic resonance spectroscopy. J Neurosci 30, 13983-13991.

Brand, A., Singer, K., Koehl, G. E., Kolitzus, M., Schoenhammer, G., Thiel, A., Matos, C., Bruss, C., Klobuch, S., Peter, K., et al. (2016). LDHA-Associated Lactic Acid Production Blunts Tumor Immunosurveillance by T and NK Cells. Cell metabolism 24, 657-671.

Brown, G. K., Otero, L. J., LeGris, M., and Brown, R. M. (1994). Pyruvate dehydrogenase deficiency. J Med Genet 31, 875-879.

Bucher, T., Brauser, B., Conze, A., Klein, F., Langguth, O., and Sies, H. (1972). State of oxidation-reduction and state of binding in the cytosolic NADH-system as disclosed by equilibration with extracellular lactate-pyruvate in hemoglobin-free perfused rat liver. Eur J Biochem 27, 301-317.

Cremer, J. E., Cunningham, V. J., Pardridge, W. M., Braun, L. D., and Oldendorf, W. H. (1979). Kinetics of blood-brain barrier transport of pyruvate, lactate and glucose in suckling, weanling and adult rats. J Neurochem 33, 439-445.

Domenech, C., Thomas, X., Chabaud, S., Baruchel, A., Gueyffier, F., Mazingue, F., Auvrignon, A., Corm, S., Dombret, H., Chevallier, P., et al. (2011). l-asparaginase loaded red blood cells in refractory or relapsing acute lymphoblastic leukaemia in children and adults: results of the GRASPALL 2005-01 randomized trial. Br J Haematol 153, 58-65.

El-Sayed, A. S., Khalaf, S. A., and Aziz, H. A. (2013). Characterization of homocysteine gamma-lyase from submerged and solid cultures of Aspergillus fumigatus ASH (JX006238). J Microbiol Biotechnol 23, 499-510.

Fischer, K., Hoffmann, P., Voelkl, S., Meidenbauer, N., Ammer, J., Edinger, M., Gottfried, E., Schwarz, S., Rothe, G., Hoves, S., et al. (2007). Inhibitory effect of tumor cell-derived lactic acid on human T cells. Blood 109, 3812-3819.

Garin, M., Rossi, L., Luque, J., and Magnani, M. (1995). Lactate catabolism by enzyme-loaded red blood cells. Biotechnol Appl Biochem 22 (Pt 3), 295-303.

Haigis, M. C., and Guarente, L. P. (2006). Mammalian sirtuins—emerging roles in physiology, aging, and calorie restriction. Genes & development 20, 2913-2921.

Halestrap, A. P. (2012). The monocarboxylate transporter family—Structure and functional characterization. IUBMB Life 64, 1-9.

Hamarat Baysal, S., and Uslan, A. H. (2001). Encapsulation of catalase and PEG-catalase in erythrocyte. Artif Cells Blood Substit Immobil Biotechnol 29, 359-366.

Hung, Y. P., Albeck, J. G., Tantama, M., and Yellen, G. (2011). Imaging cytosolic NADH-NAD(+) redox state with a genetically encoded fluorescent biosensor. Cell metabolism 14, 545-554.

Hwang, J. H., Kim, D. W., Jo, E. J., Kim, Y. K., Jo, Y. S., Park, J. H., Yoo, S. K., Park, M. K., Kwak, T. H., Kho, Y. L., et al. (2009). Pharmacological stimulation of NADH oxidation ameliorates obesity and related phenotypes in mice. Diabetes 58, 965-974.

Ihler, G., Lantzy, A., Purpura, J., and Glew, R. H. (1975). Enzymatic degradation of uric acid by uricase-loaded human erythrocytes. The Journal of clinical investigation 56, 595-602.

Jain, I. H., Zazzeron, L., Goli, R., Alexa, K., Schatzman-Bone, S., Dhillon, H., Goldberger, O., Peng, J., Shalem, O., Sanjana, N. E., et al. (2016). Hypoxia as a therapy for mitochondrial disease. Science 352, 54-61.

Kalnenieks, U., Galinina, N., Bringer-Meyer, S., and Poole, R. K. (1998). Membrane D-lactate oxidase in Zymomonas mobilis: evidence for a branched respiratory chain. FEMS Microbiol Lett 168, 91-97.

Khutornenko, A. A., Roudko, V. V., Chernyak, B. V., Vartapetian, A. B., Chumakov, P. M., and Evstafieva, A. G. (2010). Pyrimidine biosynthesis links mitochondrial respiration to the p53 pathway. Proceedings of the National Academy of Sciences of the United States of America 107, 12828-12833.

King, M. P., and Attardi, G. (1989). Human cells lacking mtDNA: repopulation with exogenous mitochondria by complementation. Science 246, 500-503.

Koivisto, H., Leinonen, H., Puurula, M., Hafez, H. S., Barrera, G. A., Stridh, M. H., Waagepetersen, H. S., Tiainen, M., Soininen, P., Zilberter, Y., et al. (2016). Chronic Pyruvate Supplementation Increases Exploratory Activity and Brain Energy Reserves in Young and Middle-Aged Mice. Front Aging Neurosci 8, 41.

Koul, D., Shen, R., Bergh, S., Sheng, X., Shishodia, S., Lafortune, T. A., Lu, Y., de Groot, J. F., Mills, G. B., and Yung, W. K. (2006). Inhibition of Akt survival pathway by a small-molecule inhibitor in human glioblastoma. Mol Cancer Ther 5, 637-644.

Kowlgi, N. G., and Chhabra, L. (2015). D-lactic acidosis: an underrecognized complication of short bowel syndrome. Gastroenterol Res Pract 2015, 476215.

Li, S. J., Umena, Y., Yorita, K., Matsuoka, T., Kita, A., Fukui, K., and Morimoto, Y. (2007). Crystallographic study on the interaction of L-lactate oxidase with pyruvate at 1.9 Angstrom resolution. Biochemical and biophysical research communications 358, 1002-1007.

Lin, S. J., Ford, E., Haigis, M., Liszt, G., and Guarente, L. (2004). Calorie restriction extends yeast life span by lowering the level of NADH. Genes & development 18, 12-16.

Ling, B., Peng, F., Alcorn, J., Lohmann, K., Bandy, B., and Zello, G. A. (2012). D-Lactate altered mitochondrial energy production in rat brain and heart but not liver. Nutr Metab (Lond) 9, 6.

Martin, A., Baker, T. A., and Sauer, R. T. (2005). Rebuilt AAA+motors reveal operating principles for ATP-fuelled machines. Nature 437, 1115-1120.

Martinus, R. D., Linnane, A. W., and Nagley, P. (1993). Growth of rho 0 human Namalwa cells lacking oxidative phosphorylation can be sustained by redox compounds potassium ferricyanide or coenzyme Q10 putatively acting through the plasma membrane oxidase. Biochem Mol Biol Int 31, 997-1005.

Mashburn, L. T., and Wriston, J. C., Jr. (1964). Tumor Inhibitory Effect of L-Asparaginase from Escherichia Coli. Arch Biochem Biophys 105, 450-452.

Melik-Adamyan, W., Bravo, J., Carpena, X., Switala, J., Mate, M. J., Fita, I., and Loewen, P. C. (2001). Substrate flow in catalases deduced from the crystal structures of active site variants of HPII from *Escherichia coli*. Proteins 44, 270-281.

Morais, R., Guertin, D., and Kornblatt, J. A. (1982). On the contribution of the mitochondrial genome to the growth of Chinese hamster embryo cells in culture. Can J Biochem 60, 290-294.

Muller, H. J., and Boos, J. (1998). Use of L-asparaginase in childhood ALL. Crit Rev Oncol Hematol 28, 97-113.

Muzykantov, V. R. (2010). Drug delivery by red blood cells: vascular carriers designed by mother nature. Expert Opin Drug Deliv 7, 403-427.

Pink, J. J., Planchon, S. M., Tagliarino, C., Varnes, M. E., Siegel, D., and Boothman, D. A. (2000). NAD(P)H:Quinone oxidoreductase activity is the principal determinant of beta-lapachone cytotoxicity. The Journal of biological chemistry 275, 5416-5424.

Pisal, D. S., Kosloski, M. P., and Balu-Iyer, S. V. (2010). Delivery of therapeutic proteins. J Pharm Sci 99, 2557-2575.

Quintana, A., Kruse, S. E., Kapur, R. P., Sanz, E., and Palmiter, R. D. (2010). Complex I deficiency due to loss of Ndufs4 in the brain results in progressive encephalopathy resembling Leigh syndrome. Proceedings of the National Academy of Sciences of the United States of America 107, 10996-11001.

Ross, J. M., Oberg, J., Brene, S., Coppotelli, G., Terzioglu, M., Pernold, K., Goiny, M., Sitnikov, R., Kehr, J., Trifunovic, A., et al. (2010). High brain lactate is a hallmark of aging and caused by a shift in the lactate dehydrogenase AB ratio. Proceedings of the National Academy of Sciences of the United States of America 107, 20087-20092.

Shaham, O., Slate, N. G., Goldberger, O., Xu, Q., Ramanathan, A., Souza, A. L., Clish, C. B., Sims, K. B., and Mootha, V. K. (2010). A plasma signature of human mitochondrial disease revealed through metabolic profiling of spent media from cultured muscle cells. Proceedings of the National Academy of Sciences of the United States of America 107, 1571-1575.

Shi, J., Kundrat, L., Pishesha, N., Bilate, A., Theile, C., Maruyama, T., Dougan, S. K., Ploegh, H. L., and Lodish, H. F. (2014). Engineered red blood cells as carriers for systemic delivery of a wide array of functional probes. Proceedings of the National Academy of Sciences of the United States of America 111, 10131-10136.

Smith, J. A., Telford, R. D., Kolbuch-Braddon, M., and Weidemann, M. J. (1997). Lactate/H+ uptake by red blood cells during exercise alters their physical properties. Eur J Appl Physiol Occup Physiol 75, 54-61.

Taurino, I. R., R.; Richterb, M.; Fairheadb, M.; Thony-Meyerb, L.; De Michelia, G.; Carrara, S. (2013). Comparative study of three lactate oxidases from *Aerococcus viridans* for biosensing applications. Electrochimica Acta 93, 72-79.

Thompson Legault, J., Strittmatter, L., Tardif, J., Sharma, R., Tremblay-Vaillancourt, V., Aubut, C., Boucher, G., Clish, C. B., Cyr, D., Daneault, C., et al. (2015). A Metabolic Signature of Mitochondrial Dysfunction Revealed through a Monogenic Form of Leigh Syndrome. Cell reports 13, 981-989.

Titov, D. V., Cracan, V., Goodman, R. P., Peng, J., Grabarek, Z., and Mootha, V. K. (2016). Complementation of mitochondrial electron transport chain by manipulation of the NAD+/NADH ratio. Science 352, 231-235.

Updike, S. J., Wakamiya, R. T., and Lightfoot, E. N., Jr. (1976). Asparaginase entrapped in red blood cells: action and survival. Science 193, 681-683.

Vafai, S. B., Meyers, E., Higgins, K. W., Fomina, Y., Zhang, J., Mandinova, A., Newman, D., Shaw, S. Y., Clardy, J., and Mootha, V. K. (2016). Natural Product Screening Reveals Naphthoquinone Complex I Bypass Factors. PloS one 11, e0162686.

Vafai, S. B., and Mootha, V. K. (2012). Mitochondrial disorders as windows into an ancient organelle. Nature 491, 374-383.

von Kleist-Retzow, J. C., Hornig-Do, H. T., Schauen, M., Eckertz, S., Dinh, T. A., Stassen, F., Lottmann, N., Bust, M., Galunska, B., Wielckens, K., et al. (2007). Impaired mitochondrial Ca2+ homeostasis in respiratory chain-deficient cells but efficient compensation of energetic disadvantage by enhanced anaerobic glycolysis due to low ATP steady state levels. Exp Cell Res 313, 3076-3089.

Williamson, D. H., Lund, P., and Krebs, H. A. (1967). The redox state of free nicotinamide-adenine dinucleotide in the cytoplasm and mitochondria of rat liver. The Biochemical journal 103, 514-527.

Williamson, J. R., Chang, K., Frangos, M., Hasan, K. S., Ido, Y., Kawamura, T., Nyengaard, J. R., van den Enden, M., Kilo, C., and Tilton, R. G. (1993). Hyperglycemic pseudo-hypoxia and diabetic complications. Diabetes 42, 801-813.

Zhao, Y., Hu, Q., Cheng, F., Su, N., Wang, A., Zou, Y., Hu, H., Chen, X., Zhou, H. M., Huang, X., et al. (2015). SoNar, a Highly Responsive NAD+/NADH Sensor, Allows High-Throughput Metabolic Screening of Anti-tumor Agents. Cell metabolism 21, 777-789.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing blood lactate levels, increasing blood pyruvate levels, and/or decreasing blood lactate/pyruvate ratio in a subject, the method comprising administering to the subject a therapeutically effective amount of:
   (i) lactate oxidase (LOX) and Catalase (CAT); or
   (ii) a fusion polypeptide comprising both LOX and CAT.

2. The method of claim 1, wherein the subject has acute lactic acidosis; D-lactic acid toxicity; a mitochondrial disorder; cancer; an ischemia-reperfusion injury; traumatic brain injury; cardiac arrest; or type 2 diabetes.

3. The method of claim 2, wherein the acute lactic acidosis is in sepsis.

4. The method of claim 2, wherein the D-lactic acid toxicity is in Short bowel syndrome.

5. The method of claim 1, wherein the administering of (i) LOX and CAT or (ii) fusion polypeptide is by (a) red blood cell (RBC) encapsulation; (b) attachment to RBC outer surface; (c) engineered bone marrow transplant; or (d) direct injection.

6. The method of claim 1, comprising administering to the subject a therapeutically effective amount of lactate oxidase (LOX) and Catalase (CAT) in a 1:1 molar ratio.

7. The method of claim 1, comprising administering a fusion polypeptide comprising LOXCAT.

8. The method of claim 7, wherein the LOXCAT fusion polypeptide is at least 90% identical to amino acids 45-1199 of SEQ ID NO:1.

9. The method of claim 7, wherein the LOXCAT fusion polypeptide comprises amino acids 45-1199 of SEQ ID NO:1.

10. The method of claim 7, wherein the LOXCAT fusion polypeptide comprises an albumin binding peptide.

11. The method of claim 1, wherein the fusion polypeptide comprises both LOX and CAT and an albumin binding peptide (ABP).

* * * * *